United States Patent
Ong et al.

(10) Patent No.: US 10,213,374 B2
(45) Date of Patent: Feb. 26, 2019

(54) ORAL CARE COMPOSITIONS AND METHODS OF USE

(71) Applicant: Colgate-Palmolive Company, New York, NY (US)

(72) Inventors: Jane Ong, Franklin Park, NJ (US); James Masters, Ringoes, NJ (US); Tatiana Brinzari, Piscataway, NJ (US); Chi-Yuan Cheng, Hillsborough, NJ (US); Donghui Wu, Bridgewater, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/791,812

(22) Filed: Oct. 24, 2017

(65) Prior Publication Data

US 2018/0110712 A1 Apr. 26, 2018

Related U.S. Application Data

(60) Provisional application No. 62/412,032, filed on Oct. 24, 2016.

(51) Int. Cl.
*A61K 8/27* (2006.01)
*A61K 8/60* (2006.01)
*A61Q 11/00* (2006.01)
*A61K 8/49* (2006.01)

(52) U.S. Cl.
CPC ............ *A61K 8/602* (2013.01); *A61K 8/27* (2013.01); *A61K 8/498* (2013.01); *A61Q 11/00* (2013.01); *A61K 2800/51* (2013.01); *A61K 2800/58* (2013.01)

(58) Field of Classification Search
None
See application file for complete search history.

(56) References Cited

FOREIGN PATENT DOCUMENTS

| CN | 102218021 | 10/2011 |
|---|---|---|
| CN | 105232388 A | 1/2016 |
| WO | 2015027308 | 3/2015 |

OTHER PUBLICATIONS

International Search Report and Written Opinion of the International Searching Authority in International Application No. PCT/US2017/057997, dated Jan. 5, 2018.
Sarria et al., 2016, "Copper (II) and zinc (II) complexes with flavanone derivatives: Identification of potential cholinesterase inhibitors by on-flow assays," J. Inorganic Biochemistry 164:141-149.
Al-Hassani et al., 2015, "Synthesis, Characterization, Theoretical Studies and Biological Activities of Naringin Metal Complexes," Acta Chimica & Pharmaceutica Indica 5(3):129-142.
Ang et al., 2011, "Naringin abrogates osteoclastogenesis and bone resorption via the inhibition of RANKL-induced NF-KB and ERK activation," FEBS Letters 585(17):2755-2762.
Bharti et al., 2014, "Preclinical Evidence for the Pharmacological Actions of Naringin: A Review," Planta Medica 80 (6):437-451.
Brandt, 2013, "The clinical effects of zinc as a topical or oral agent on the clinical response and pathophysiologic mechanisms of acne: a systematic review of the literature," J. Drugs Dermatol. 12(5):542-545.
Darby et al., 2001, "Microbiology of periodontal disease in children and young adults," Periodontology 2000 26:33-53.
Epasinghe et al., 2016, "Effect of Flavonoids on Remineralization of Artificial Root Caries," Australian Dental Journal 61(2):196-202.
Kandhare et al., 2014, "Naringin, a Flavanone Glycoside, Promotes Angiogenesis and Inhibits Endothelial Apoptosis Through Modulation of Inflammatory and Growth Factor Expression in Diabetic Foot Ulcer in Rats," Chemico-Biological Interactions 219:101-112.
Kiefer et al., 2010, "Citrus Flavonoids with Skin Lightening Effects—Safety and Efficacy Studies," SOFW Journal Dec. 2010 pp. 45-54.
Kuntic et al., 1998, "Spectrophotometric Investigation of Uranil(II)-Rutin Complex in 70 Ethanol," J. Agric. Food Chem. 46(12):5139-5142.
Li et al., 2014, "The remineralisation of enamel: a review of the literature," J. of Dentistry 42:S12-S20.
Li et al., 2007, "Infrared and DNA-binding on ultraviolet and fluorescence spectra of new copper and zinc complexes with a naringenin Schiff-base ligand," Spectrochimica Acta Part A 67(2):395-401.
Malesev et al., 2007, "Investigation of metal-?flavonoid chelates and the determination of flavonoids via metal-?flavonoid complexing reactions," J. Serb. Chem. Soc. 72(10):921-939.
Misiak et al., 2010, "Interactions of Flavonoids with Transition Metal Ions," Pharmaceuticals 39-42.
Pereira et al., 2007, "Synthesis and Characterization of a Metal Complex Containing Naringin and Cu, and its Antioxidant, Antimicrobial, Antiinflammatory and Tumor Cell Cytotoxicity," Molecules12(7):1352-1366.
Selvaraj, 2014, "Investigations on the Membrane Interactions of Narignin and its Complexes with Copper and Iron: Implications for Their Cytotoxicity," RSC Advances4(87):46407-46417.
Toledano et al., 2012, "Zinc-Inhibited MMP-Mediated Collagen Degradation after Different Dentine Demineralization Procedures," Caries Research 46(3):201-207.
Tsui et al., 2008, "The inhibitory effects of naringin on the growth of periodontal pathogens in vitro," Phytotherapy Research 22(3):401-406.
Yousuf, 2014, "Binding of the Bi (III) Complex of Naringin with β-Cyclodextrin/Calf Thymus DNA: Absorption and Fluorescence Characteristics," Intl Journal of Spectroscopy, Article ID 562160.

*Primary Examiner* — Nannette Holloman

(57) ABSTRACT

Disclosed herein are oral care compositions comprising naringin:Zinc complexes having a 2:1 naringin to zinc molar ratio. Methods of making and using the compositions are also provided.

20 Claims, 23 Drawing Sheets

ORAL CARE COMPOSITIONS AND METHODS OF USE

CROSS REFERENCE TO RELATED APPLICATIONS

This application claims priority to U.S. Application Ser. No. 62/412,032, filed on Oct. 24, 2016, the content of which is expressly incorporated herein by reference.

FIELD

This invention relates to oral care compositions comprising Naringin:Zinc complexes as well as to methods of using and of making these compositions.

BACKGROUND

Naringin is a flavanone glycoside, commonly found in grapefruits and citrus fruits. It has been documented to exhibit health benefits on diverse applications, such as antimicrobial activities (Pereira R. et al., Molecules, 2007, 12: 1352-66; Abdulmahdi A-H. et al., Acta Chimica & Pharmaceutica Indica, 2015, 5(3): 129-42), wound healing (Kandhare A. D. et al., Chemico-Biological Interactions, 2014, 219: 101-12, Pereira R. et al., supra, Abdulmahdi A-H. et al., supra), periodontal diseases, diabetes mellitus and rheumatological disorders (Tsui V. W. K. et al., Phytotherapy Research, 2008, 22(3): 401-406; Bharti S. et al., Planta Med, 2014, 80: 437-51). Furthermore, it was demonstrated to inhibit the growth of periodontal pathogens as well as some common oral microorganisms in vitro (Tsui V. W. K. et al., supra).

Tooth demineralization is a chemical process by which minerals, mainly calcium, are removed from any of the hard tissues, i.e. enamel, dentine, and cementum (X Li et al., J. of Dentistry, 2014, 42:S12-20). Effects of demineralization may be reversed if there is sufficient time to allow remineralization to occur to counteract the acids in the oral cavity. Remineralization is beneficial for the aging population who experience gum recession as well as patients with severe periodontitis with obvious root exposure. Remineralization may further offer protection against cavity progression. A remineralization effect of flavonoids, including Naringin, on artificial root caries is reported; however; the flavonoids showed to be less effective than fluoride (Epasinghe D. J. et al., Australian Dental Journal, 2016, 61(2): 196-202).

Matrix metalloproteinases (MMPs) have been suggested to play an important role in the destruction of dentine organic matrix following demineralization by bacterial acids. Increasing Zinc concentration has been shown to inhibit dentine-MMP dependent collagen degradation (Toledano M. et al., Caries Res., 2012, 46(3):201-207).

Naringin and Zinc citrate have previously been combined in a toothpaste formulation; see CN102218021, published Jan. 23, 2013. Naringin-metal complexes for use in insecticide compositions have been described in WO2015027308, published Mar. 3, 2015. Naringin-metal complexes have been previously disclosed (Al-Hassani R. A. et al., Acta Chimica & Pharmaceutica Indica, 2015, 5(3): 129-42); however, synthesis of such complexes utilized ethanol solutions, which is not optimal as an ingredient for use in consumer products. Therefore, methods of synthesis are needed for enhanced production of such molecules.

Current oral care market products do not address gum recession benefits. Accordingly, there is a need for oral compositions to treat and/or prevent progression of gum recession.

SUMMARY OF THE INVENTION

It has been surprisingly found that complexes of naringin and zinc having two moles of naringin to one mole of zinc may be produced. These complexes show unexpected physical-chemical attributes, such as an increase in antibacterial activity. Such activity may be useful for use in oral care compositions.

In one embodiment, the invention is a naringin:Zn complex, wherein the naringin:Zn complex has a 2:1 naringin to zinc molar ratio. In a further embodiment, the naringin:Zinc complex has a melting point above 230° C. In further embodiments, the naringin:Zinc complex has a diffusion coefficient between 2.8e-11 to 3.2e-11 $m^2/s$ in DMSO solution at 25° C.

In a particular embodiment, the invention provides an oral care composition comprising the naringin:Zinc complex. In certain embodiments, the oral care composition may be selected from the group consisting of: a toothpaste or a dentifrice, a mouthwash or a mouth rinse, a topical oral gel and a denture cleanser. In certain embodiments, the oral care composition may be selected from dental strips, beads, varnish and toothpowder.

In certain embodiments, a composition of the invention may further comprise one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, anticalculus or tartar control agents, and mixtures thereof.

In one embodiment, the invention provides a method to improve oral health comprising applying an effective amount of the oral composition described herein to the oral cavity of a subject in need thereof. In certain embodiments, the oral health may be selected from one or more of the following: reduce or inhibit formation of dental caries; reduce, repair or inhibit early enamel lesions; reduce or inhibit demineralization and promote remineralization of the teeth; reduce hypersensitivity of the teeth; reduce or inhibit gingivitis; promote healing of sores or cuts in the mouth; reduce levels of acid producing bacteria; increase relative levels of arginolytic bacteria; inhibit microbial biofilm formation in the oral cavity; raise and/or maintain plaque pH at levels of at least pH 5.5 following sugar challenge; reduce plaque accumulation; treat, relieve or reduce dry mouth; whiten teeth; enhance systemic health, including cardiovascular health; reduce erosion of the teeth; immunize the teeth against cariogenic bacteria and their effects; clean the teeth and oral cavity; reduce inflammation; and increase antioxidant levels.

In further embodiments, the invention provides for methods for preparing a naringin:Zinc complex having a 2:1 naringin to zinc molar ratio. In certain embodiments, the method includes a complex preparation step performed using a pH between 7-10. In certain embodiments, the method includes mixing of naringin and zinc at a temperature between 65-85° C.

In certain embodiments, the method of preparing the 2:1 naringin:zinc complex comprises the steps of mixing naringin in methanol; adding a source of zinc; adjusting the pH of the solution to 10.0; incubating the reaction; and optionally isolating the complex. In other embodiments, the method comprises the steps of mixing naringin in water; heating the mixture to 70° C.; adding a source of zinc; adjusting the pH of the solution to 10.0; incubating the reaction; and optionally isolating the complex. In other embodiments, the method comprises the steps of mixing naringin in water; heating the mixture to 70° C.; adjusting the pH of the solution to 10.0; adding a source of zinc; and optionally isolating the complex. In other embodiments, the method comprises the steps of mixing naringin in water; heating the mixture to 70° C.; adding a source of zinc; adjusting the pH of the solution to 7.0; and optionally isolating the complex. In certain embodiments, the method comprises the steps of mixing naringin and ZnO in water; heating the mixture; incubating the mixture; and optionally isolating the complex. In certain embodiments, the method comprises mixing naringin in propylene glycol at 70° C.; adjusting the pH of the solution to be between 9.0-10.0; adding a source of zinc in propylene glycol at 40-50° C.; and optionally isolating the complex.

In certain embodiments, the Zn source is selected from zinc acetate, zinc oxide, zinc chloride, zinc lactate, zinc citrate, or zinc nitrate. In certain embodiments, the Zn source is zinc acetate. In certain embodiments, the Zn source is ZnO.

In certain embodiments, the invention is a composition obtained or obtainable by combining the ingredients as set forth in any of the preceding compositions and methods.

DETAILED DESCRIPTION

Figure 1A:
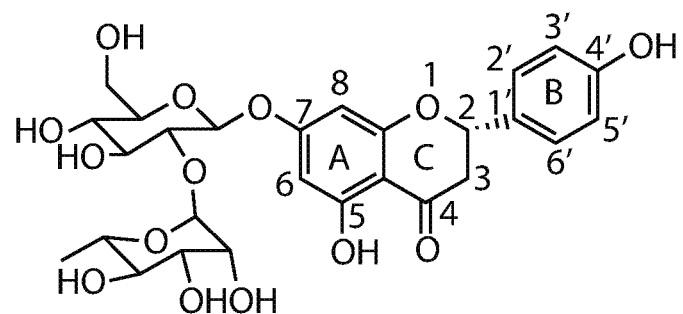
FIG. 1A is the molecular structure of Naringin.
Figure 1B:
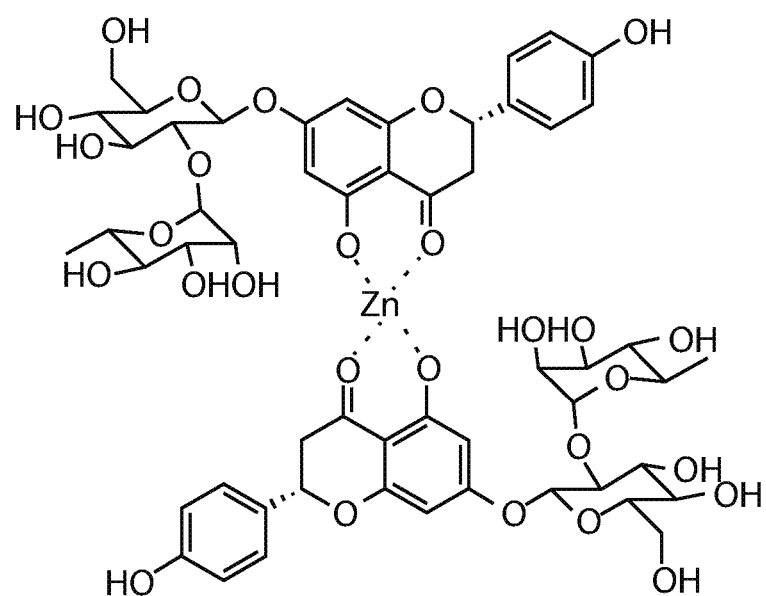
FIG. 1B is the proposed molecular structure for 2:1 naringin:Zinc complex.

The following description of embodiment(s) of the invention is merely exemplary in nature and is in no way intended to limit the invention, its application, or uses.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range.

Unless stated otherwise, all percentages of composition components given in this specification are by weight based on a total composition or formulation weight of 100%.

All references cited herein are hereby incorporated by reference in their entireties. In the event of a conflict in a definition in the present disclosure and that of a cited reference, the present disclosure controls.

As used herein, the term "oral composition" means the total composition that is delivered to the oral surfaces. The composition is further defined as a product which, during the normal course of usage, is not for the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, dental strips, beads, varnish, toothpowder and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

The term "mouthrinse" in the present invention refers to oral compositions that are substantially liquid in character, such as a mouth wash, spray, or rinse. In such a preparation the orally acceptable carrier typically has an aqueous phase comprising water or a water and alcohol mixture. Further, in various embodiments, the oral carrier includes a humectant and surfactant as described below. Generally, the weight ratio of water to alcohol is in the range of in an amount of 1:1 to 20:1, preferably 3:1 to 10:1 and more preferably 4:1 to 6:1. The total amount of water-alcohol mixture in this type of preparation is typically in an amount of 70 to 99.9% of the preparation. In various embodiments, the alcohol is typically ethanol or isopropanol.

The term "effective amount" as used herein means that the amount of the composition of the present invention is of sufficient quantity to achieve the intended purpose, such as, for example, to induce or cause remineralization in the subject.

The terms "2:1 naringin:Zn", "2:1 naringin:Zn complex", "naringin:zinc" and "naringin:zinc complex" are used interchangeably and refer, unless specified otherwise, to the complex of the invention.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "cosmetically acceptable" is meant suitable for use in a formulation for topical application to human skin. A cosmetically acceptable excipient, for example, is an excipient which is suitable for external application in the amounts and concentrations contemplated in the formulations of this invention, and includes for example, excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

The invention provides for compositions comprising naringin:Zn complex(es), wherein the naringin:Zn complex has a 2:1 naringin to zinc molar ratio. Such complexes provide unique features, such as enhanced antimicrobial activities, useful in oral care applications.

In some embodiments, the present invention provides complexes of naringin:zinc having a melting point of at least 200° C., 205° C., 210° C., 215° C., 220° C., 225° C., 230° C., 235° C., 240° C., 245° C., or 250° C. In some embodiments, the present invention provides complexes of naringin:zinc having a melting point of about 200° C., 205° C., 210° C., 215° C., 220° C., 225° C., 230° C., 235° C., 240° C., 245° C., or 250° C.

The invention further provides for methods of preparing a naringin:Zn complex having a 2:1 naringin to zinc molar ratio. In certain preferred embodiments, the naringin and zinc source are combined at a pH between 7-10. In certain embodiments, the naringin and zinc source are combined at a pH between 8-10. In certain embodiments, the naringin and zinc source are combined at a pH between 9-10. In certain embodiments, the naringin and zinc source are combined at a pH of about 7. In certain embodiments, the naringin and zinc source are combined at a pH of about 8. In certain embodiments, the naringin and zinc source are combined at a pH of about 9. In certain embodiments, the naringin and zinc source are combined at a pH of about 10.

In certain embodiments, the complex is synthesized at a temperature between 20° C. to 80° C. In certain embodiments, the complex is synthesized at a temperature between 25° C. to 75° C. In certain embodiments, the complex is synthesized at a temperature between 30° C. to 70° C. In certain embodiments, the complex is synthesized at a temperature between 35° C. to 65° C. In certain embodiments, the complex is synthesized at a temperature between 20° C. to 40° C. In certain embodiments, the complex is synthesized at a temperature between 40° C. to 60° C. In certain embodiments, the complex is synthesized at a temperature between 60° C. to 80° C. In certain embodiments, the complex is synthesized at a temperature between 20° C. to 25° C.

In certain embodiments, the complex is synthesized at a temperature between 20° C. to 80° C. and a pH between 7-10. In certain embodiments, the complex is synthesized at a temperature between 25° C. to 75° C. and a pH between 7-10. In certain embodiments, the complex is synthesized at a temperature between 30° C. to 70° C. and a pH between 7-10.

In certain embodiments, the method of preparing the 2:1 naringin:zinc complex comprises the steps of mixing naringin in methanol; adding a source of zinc; adjusting the pH of the solution to about 10.0; incubating the reaction; and optionally isolating the complex. In other embodiments, the method comprises the steps of mixing naringin in water; heating the mixture to about 70° C.; adding a source of zinc; adjusting the pH of the solution to about 10.0; incubating the reaction; and optionally isolating the complex. In other embodiments, the method comprises the steps of mixing naringin in water; heating the mixture to about 70° C.; adjusting the pH of the solution to about 10.0; adding a source of zinc; and optionally isolating the complex. In other embodiments, the method comprises the steps of mixing naringin in water; heating the mixture to about 70° C.; adding a source of zinc; adjusting the pH of the solution to about 7.0; and optionally isolating the complex. In certain embodiments, the method comprises the steps of mixing naringin and ZnO in water; heating the mixture; incubating the mixture; and optionally isolating the complex. In certain embodiments, the method comprises mixing naringin in propylene glycol at about 70° C.; adjusting the pH of the solution to be between 9.0-10.0; adding a source of zinc in propylene glycol at about 40-50° C.; and optionally isolating the complex.

The invention further provides the use of a composition comprising the 2:1 naringin:zinc complex to reduce and/or inhibit acid erosion of the enamel, reducing or inhibiting gum recession, controlling microbial growth, clean the teeth, reduce bacterially-generated biofilm and plaque, reduce gingivitis, inhibit tooth decay and formation of cavities, and/or reduce dentinal hypersensitivity. The invention provides the use of a composition comprising the 2:1 naringin:Zinc complex for wound healing. The invention further provides for use of a composition comprising the 2:1 naringin:Zinc complex for ameliorating and/or preventing inflammation. The invention further provides for use of a composition comprising the 2:1 naringin:Zinc complex for ameliorating and/or preventing bleeding.

In certain embodiments, naringin:zinc complexes are included in oral care compositions. In some embodiments, the oral care composition may be selected from the group selected from a toothpaste or a dentifrice, a mouthwash or a mouth rinse, a topical oral gel and a denture cleanser. In some embodiments, the oral care composition may be toothpaste or a dentifrice. In some embodiments, the oral care composition may be a mouthwash or a mouth rinse. In some embodiments, the oral care composition may be a topical oral gel and a denture cleanser.

In further embodiments, the invention is a method to improve oral health comprising applying an effective amount of an oral composition described herein to the oral cavity of a subject in need thereof. In certain embodiments, the method includes use of a 2:1 naringin:zinc complex composition selected from the group consisting of a toothpaste or a dentifrice, a mouthwash or a mouth rinse, a topical oral gel and a denture cleanser.

The invention further provides methods to reduce and inhibit acid erosion of the enamel, reducing or inhibiting gum recession, controlling microbial growth, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of said compositions described herein, to the teeth.

For example, the invention provides methods to reduce and inhibit acid erosion of the enamel, reducing or inhibiting gum recession, controlling microbial growth, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of said compositions described herein, to the oral cavity, and then rinsing with sufficient water or aqueous solution.

In certain embodiments, the complex is included in a mouthwash. In some embodiments, the mouthwash comprises from 0.002% to 4% zinc, by weight. In some embodiments, the mouthwash comprises from 0.005% to 0.01% zinc, by weight. In some embodiments, the mouthwash comprises from 0.01% to 1% zinc, by weight. In some embodiments, the mouthwash comprises from 1% to 4% zinc, by weight. In some embodiments, the mouthwash of any of the foregoing has zinc solubilized in the formulation, which provides a zinc source upon mixing with a naringin containing solution upon use and dilution with saliva and/or rinsing. In other embodiments, the zinc ion source and the naringin source form a naringin:zinc complex.

In some embodiments, the pH of the mouthwash is from pH 4 to pH 8.

Some embodiments further comprise an effective amount of a fluoride ion source within the composition.

In other embodiments, the invention comprises an orally acceptable base comprising ingredients selected from one or more of buffering agents, humectants, surfactants, thickeners, breath fresheners, flavoring, fragrance, coloring, antibacterial agents, whitening agents, agents that interfere with or prevent bacterial attachment, calcium sources, phosphate sources, orally acceptable potassium salts, and anionic polymers.

Some embodiments provide a mouthwash for use in reducing or inhibiting acid erosion of the enamel, reducing or inhibiting gum recession, controlling microbial growth, cleaning the teeth, reducing bacterially-generated biofilm and plaque, reducing gingivitis, inhibiting tooth decay and formation of cavities, and/or reducing dentinal hypersensitivity.

Some embodiments provide the use of a 2:1 naringin:zinc complex for the manufacture of a mouthwash. Other embodiments provide a method of treating or reducing dental enamel erosion cleaning the teeth, reducing or inhibiting gum recession, reducing bacterially-generated biofilm and plaque, reducing gingivitis, inhibiting tooth decay and formation of cavities, and/or reducing dentinal hypersensitivity comprising applying a mouthwash as described herein. Other embodiments provide methods further comprising the step of rinsing with sufficient water or aqueous solution.

The invention further provides a method of making an oral care composition comprising combining naringin and a zinc source in an aqueous medium, optionally isolating the complex thus formed in solid form, and combining the naringin:zinc complex with an oral care composition. In certain embodiments, the oral care composition is a toothpaste. In certain embodiments, the oral care is a mouthwash base.

In various embodiments, the invention provides methods to (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of said compositions described herein to the oral cavity of a person in need thereof, e.g., one or more times per day. In further embodiments, the invention provides methods to reduce or inhibit gum recession. In further embodiments, the invention provides methods to control microbial growth. In further embodiments, the invention provides methods to reducing bacterially-generated biofilm, malodor and/orF plaque. The invention further provides any of the compositions described herein for use in any of these methods.

"Actives," means compounds that, when applied to a target tissue, provide a benefit or improvement to the target tissue. The actives can be delivered in the form of any oral care formulations, for example a toothpaste, transparent paste, gel, mouthwash, powder, cream, strip, spray, gum, or any other known in the art.

If the complex is delivered in the form of a mouthwash, a person desiring the benefits rinses with the solution containing the naringin:zinc complex. In certain embodiments, a dual chamber may be implemented. In such aspects, a first chamber contains naringin in solution at a basic pH. In certain embodiments, the pH is between 7-10. In certain embodiments, the pH is between 7-8. In certain embodiments, the pH is between 8-9. In certain embodiments, the pH is between 9-10. The dual chamber will also contain a second chamber containing a solubilized zinc source. Upon application, the contents of the first and second chamber are mixed together, thus producing the naringin:Zinc complex.

In another embodiment, the mixture is prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel. In certain embodiments, the complex is formulated in a composition comprising Carbopol® polymer, glycerin and water.

In another embodiment, the stock solution, or a mixture of stock solution with water, is applied to the teeth in a gel formulation, e.g., wherein the gel can stay on the tooth for an extended period of time for effective treatment.

In another embodiment, the composition of the present invention is a viscous liquid, preferably a gel, which maintains its consistency during storage enabling the product to be painted on the tooth surface with a soft applicator pen or brush. Some embodiments provide a method utilizing an applicator to deliver the composition, wherein the applicator is a pen and the pen is stored within an oral care implement. In some embodiments, the pen is removed from the oral care implement prior to application of the composition to the tooth. In some embodiments, the composition is applied to the tooth after brushing. In some embodiments, the composition is applied to the tooth after brushing with the oral care implement.

The zinc ion source for complex synthesis may be from any source that provides $Zn^{2+}$ ions efficiently, for example zinc oxide, zinc acetate, zinc chloride, zinc lactate, tetrabasic zinc chloride, zinc carbonate, zinc nitrate, zinc citrate, zinc bis lysinate, and zinc phosphate. Zinc oxide is a white powder, insoluble in water. Tetrabasic zinc chloride (TBZC) or zinc chloride hydroxide monohydrate is a zinc hydroxy compound with the formula $Zn_5(OH)_8Cl_2.H_2O$, also referred to as basic zinc chloride, zinc hydroxychloride, or zinc oxychloride. It is a colorless crystalline solid insoluble in water. Both of these materials may be solubilized in water in the presence of naringin and heat, thus providing a source of zinc ions. In certain preferred embodiments, the Zn source is selected from zinc acetate, zinc oxide, zinc chloride, zinc lactate, zinc citrate, or zinc nitrate.

In certain embodiments, the amount of zinc in the composition is 0.005 to 30% by weight of the composition. In certain embodiments, precursors, e.g., zinc sources and naringin, are present in amounts such that when combined into the naringin:zinc complex, the complex would be present in an amount of 0.005 to 10% by weight of the composition. In either of these embodiments, the amount of the 2:1 naringin:zinc complex can be varied for the desired purpose, such as a dentifrice or a mouthwash. In other embodiments, the amount of the 2:1 naringin:zinc complex is at least 0.1, at least 0.2, at least 0.3, at least 0.4, at least 0.5, at least 1, at least 2, at least 3, or at least 4 up to 10% by weight of the composition. In other embodiments, the amount of the 2:1 naringin:zinc complex is less than 9, less than 8, less than 7, less than 6, less than 5, less than 4, less than 3, less than 2, less than 1, less than 0.5 to 0.005% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., naringin and zinc sources, will not significantly react to form the 2:1 naringin:zinc complex. When contacted with a sufficient amount of water, which can be in the form of saliva and/or water used to rinse the mouth during or after application of the composition, the precursors will then react to form the 2:1 naringin:zinc complex. In preferred embodiments, the water and/or saliva has a pH between 7-10. In certain embodiments, the pH is between 7-9. In certain embodiments, the pH is between 7-8.

In certain embodiments, oral care compositions having naringin:zinc complexes further comprise one or more agents selected from diluents, bicarbonate salts, pH modifying agents, surfactants, foam modulators, additional thickening agents, humectants, sweeteners, flavorants, pigments, antibacterial agents, anticaries agents, fluoride ion sources, anticalculus or tartar control agents, and mixtures thereof.

The oral composition according to the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerine, sorbitol, polyethylene glycols. Poloxamer polymers such as POLOXOMER® 407, PLURONIC® F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients found in magnolia extract or synthetic analogues thereof, as well as with other ingredients of the composition.

Flavorants among those useful herein include any material or mixture of materials operable to enhance the taste of the composition. Any orally acceptable natural or synthetic. flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate) peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methane glycerol acetal (MGA) and mixtures thereof. One or more flavorants are optionally present in a total amount of 0.01% to 5%, optionally in various embodiments from 0.05 to 2%, from 0.1% to 2.5%, and from 0.1 to 0.5%.

Sweetening agents among those useful herein include dextrose, polydextrose, sucrose, maltose, dextrin, dried invert sugar, mannose, xylose, ribose, fructose, levulose galactose, corn syrup, partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition of the invention.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001% to 20%, for example 0.01% to 10% or 0.1% to 5%.

Active Agents:

The compositions of the invention may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 weight % (expressed as weight of free base), e.g., about 1 to about 10 weight % for a consumer toothpaste or about 7 to about 20 weight % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 weight % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 weight % to about 10 weight % in one embodiment or about 0.03 weight % to about 5 weight %, and in another embodiment about 0.1 weight % to about 1 weight 0% by weight of the composition in another embodiment. Weights of fluoride salts to provide the appropriate level of fluoride ion will obviously vary based on the weight of the counterion in the salt.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Tartar Control Agents:

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, P1-6 phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P3O_{10}$), e.g., in proportions of TSPP at about 1-2% and STPP at about 7% to about 10/o. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Polymers:

The oral care compositions of the invention may also include additional polymers to adjust the viscosity of the formulation or enhance the solubility of other ingredients. Such additional polymers include polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139(M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alphabeta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

The composition can be any type of composition. In certain embodiments, the composition is any composition in which it is desired to include an antibacterial agent for application to the skin. Examples of such compositions include, but are not limited to, personal care compositions, antiperspirants, deodorants, body washes, shower gels, bar soaps, shampoo, hair conditioners and cosmetics.

Basic Amino Acids:

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

Suitable salts include salts known in the art to be pharmaceutically acceptable salts and are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In certain embodiments, the basic amino acid is present in an amount corresponding to 0.1% to 150%/, e.g., 0.1 weight % to 10 weight %, e.g., 0.1 to 5 wt %, e.g., 0.5 weight % to 3 weight % of the total composition weight, about e.g., 1%, 1.5%, 2%, 3%, 4%, 5%, or 8%, wherein the weight of the basic amino acid is calculated as free form.

Surfactants:

The invention may, in some embodiments, contain anionic surfactants, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate ($CH_3(CH_2)_{10}CH_2(OCH_2CH_2)_2OSO_3Na$); higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents:

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1.5% by weight.

Chelating and Anti-Calculus Agents:

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 weight % pyrophosphate ions, e.g., 0.1 to 3 wt 5, e.g., 0.1 to 2 weight %, e.g., 0.1 to 1 wt %, e.g., 0.2 to 0.5 wt %. The pyrophosphates also contribute to preservation of the compositions by lowering water activity.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Silica may also be available as a thickening agent, e.g., synthetic amorphous silica. Colloidal magnesium aluminum silicate or finely divided silica can be used as component of the thickening composition to further improve the composition's texture. In certain embodiments, thickening agents in an amount of about 0.5% to about 5.0% by weight of the total composition are used. Thickeners may be present in an amount of from 1 weight % to 15 weight %, from 3 weight % to 10 weight %, 4 weight % to 9 weight %, from 5 weight % to 8 weight %, for example 5 weight %, 6 weight %, 7 weight %, or 8 weight %.

Abrasives:

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example, a small particle silica may have an average particle size (D50) of 2.5-4.5 microns. Simply because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($Ca_3HPO_4.2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof.

In certain embodiments, any silica suitable for oral care compositions may be used, such as precipitated silicas or silica gels. For example, the silica can also be small particle silica (e.g., Sorbosil AC43 from PQ, Warrington, United Kingdom). The composition preferable contains from 5 to 20 weight % small particle silica, or for example 10-15 weight %, or for example 5 weight %, 10 wt %, 15 weight % or 20 weight % small particle silica.

In another embodiment, the abrasive may be high cleaning precipitated silica having a pellicle cleaning ratio (PCR) of greater than 85 when tested at 200% loading is known in the art as high cleaning silica. Typically, high cleaning silica also has a mean particle size $d_{50}$ of from 5 to 15 μm and an oil absorption of from 40 to 120 $cm^3$/100 g silica. The cleaning efficacy of the precipitated silica is expressed using the pellicle cleaning ratio (PCR). This is typically measured at 20% silica loading. The high cleaning silica preferably has a PCR value of greater than 85. The efficacy of the precipitated silica can also be expressed with reference to its abrasive characteristic using the radioactive dentin abrasion (RDA). Ideally, RDA values for an oral composition should be below about 250 to protect tooth enamel/dentin. Methods of performing PCR and RDA are described in e.g., U.S. Pat. Nos. 5,939,051 and 6,290,933 and "In Vitro Removal of Stain With Dentifrice", G. K. Stookey et al., *J. Dental Research*, Vol. 61, pages 1236-9, November 1982. Typically, the precipitated silica has a mean particle size $d_{50}$ of from 5 to 15 μm and an oil absorption of from 40 to 120 $cm^3$/100 g silica. Examples of precipitated silica having a mean particle size $d_{50}$ of from 5 to 15 μm and an oil absorption of from 40 to 120 $cm^3$/100 g silica including commercially available silicas such as Zeodent® 103 and Zeodent® 105 (Huber Silica Americas).

The composition preferable contains from 3 to 20 weight % high cleaning precipitated silica, or for example 10-15 weight %, or for example 5 weight %, 10 wt %, 15 weight % or 20 weight % high cleaning precipitated silica.

The composition may also comprise an abrasive silica having an acid pH in the composition. For example, prophy silica available from Grace, offered as Sylodent™, can be used. The acidic silica abrasive is included in the dentifrice components at a concentration of about 2 to about 35% by weight; about 3 to about 20% by weight, about 3 to about 15% by weight, about 10 to about 15% by weight. In certain embodiments, the acidic silica abrasive may be present in an amount between 2-7%. In other embodiments, it may be present in an amount between 7-15% by weight. Still on other embodiments, it may be present in an amount between 15-30% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %,15 wt. %, 16 wt. %, 17 wt. %, 18 wt. %, 19 wt. %, 20 wt. %.

A commercially available acidic silica abrasive is Sylodent 783 available from W.R. Grace & Company (Baltimore, Md.). Sylodent 783 has a pH of 3.4-4.2 when measured as a 5% by weight slurry in water. For use in the present invention, the silica material has an average particle size of less than 10 microns, e.g., 3-7 microns, e.g. about 5.5 microns.

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, dipotassium phosphate, tribasic sodium phosphate, sodium tripolyphosphate, phosphoric acid), citrates (e.g. citric acid, trisodium citrate dehydrate), pyrophosphates (sodium and potassium salts) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, xylitol, sodium cyclamate, perillartine, AMP (aspartyl phenyl alanine, methyl ester), saccharine and the like. Suitably, flavor and sweetening agents may each or together comprise from about 0.1% to 5% more of the preparation. Moreover, flavoring oil is believed to aid the dissolving of the antibacterial agent, together with or even in the absence of surface-active agent.

The present invention in its method aspect involves applying to the oral cavity a safe and effective amount of the compositions described herein.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Methods and Materials:

Naringin was obtained from Perfect Health, LLC (Lot CYPD-A-01468, 99% HPLC purity, Somerset, N.J.) or Sigma-Aldrich (St. Louis, Mo.) cat #71162 or N1376. Zinc (II) Acetate salt was obtained from Sigma-Aldrich (St. Louis, Mo.) cat #383317.

Example 1—Synthesis Method 1

Briefly, 1.25e-4 moles of Naringin (ligand) solution was prepared in 10 ml of methanol (J. T. Baker, cat #9093-03). Next, a 2 ml solution of Zinc (II) Acetate (1.25e-4 moles) in distilled water was slowly added with constant stirring. The pH of the solution was adjusted to around 10.0 using sodium hydroxide (50% solution) (J. T. Baker, Center Valley, Pa., cat #9721-02). The reaction was allowed to continue for around 4 hours at room temperature. The precipitate was filtered in a vacuum system, washed with water and then air dried. The naringin:Zinc complex, observed as a yellowish colored precipitate, was obtained, characterized using UV-VIS, FTIR and $^1$H NMR and labeled as Product 1.

Example 2—Synthesis Method 2

Firstly, 1.25e-4 moles of Naringin (ligand) solution was prepared in 10 ml of double distilled $H_2O$ and heated to around 70° C. to enhance the solubility of Naringin. The resultant solution was then filtered. Next, 2 ml of Zinc (II) Acetate (1.25e-4 moles) in double distilled water was slowly added under constant stirring. The pH of the solution was then adjusted to around 10.0 using sodium hydroxide (50% solution). The reaction was allowed to incubate for around 2 hours. The formed precipitate was collected, washed initially with $dDH_2O$ followed by 200 proof Ethanol. The precipitate, observed as yellowish colored, was then vacuum dried, collected, characterized using UV-Vis spectroscopy, FTIR and $^1$H-NMR and labeled as Product 2.

Example 3—Synthesis Method 3

Briefly, 1.25e-4 moles of Naringin (ligand) solution was prepared in 10 ml of double distilled $H_2O$ and heated to around 70° C. to enhance the solubility of Naringin. The pH of the solution was adjusted to around 10.0 using sodium hydroxide (50% solution). Next, 2 ml of Zinc (II) Acetate (1.25e-4 moles) in double distilled water was slowly added under constant stirring. The precipitate formed, observed as yellowish colored, was collected, washed initially with $dDH_2O$ followed by 200 proof Ethanol, vacuum dried, characterized using UV-Vis spectroscopy, FTIR and $^1$H-NMR and labeled as Product 3.

Example 4—Synthesis Method 4

Either 1.25e-4 moles or 2.50e-4 moles of Naringin (ligand) solution was prepared in 10 ml of double distilled $H_2O$ and heated to around 70° C. to enhance the solubility of Naringin. The resultant solution was filtered. Next, 2 ml solution of Zinc (II) Acetate (1.25e-4 moles) in double distilled water was slowly added under constant stirring. The pH of the solution was then adjusted to around 7.0 using sodium hydroxide (50% solution). The precipitate formed was collected, washed initially with $dDH_2O$ followed by 200 proof ethanol. The resulting precipitate, observed as yellowish colored, was vacuum dried, collected, characterized using UV-Vis spectroscopy, FTIR and $^1$H-NMR and labeled as Product 4 (1.25e-4 moles Naringin) and 5 (2.50e-4 moles Naringin).

Example 5—Synthesis Method 5

To produce a Product 6, 2.50e-4 moles of Naringin (ligand) solution was prepared in 10 ml of 7% Propylene Glycol solution pre-warmed to around 70° C. Without being bound to theory, it is believed that this temperature enhances the solubility of Naringin. The mixture (slightly cloudy and yellowish in color) was constantly stirred over a heated stirring plate maintained at 45° C. In certain embodiments, the temperature range can be 40-50° C. The pH of the solution was adjusted using sodium hydroxide until a clear orange color solution was obtained (pH 9-10). Next, 2 ml of Zinc (II) Acetate (1.25e-4 moles) in 7% Propylene Glycol solution, pre-warmed to around 70° C., was slowly added with constant stirring. The reaction was incubated for approximately 2 hours. A precipitate formed, was collected, washed initially with $dDH_2O$, then with 200 proof ethanol.

Example 6—Characterization with UV-Vis

The UV-Vis spectra of naringin:Zinc complexes were generated using a SpectraMax M5 Plate Reader. Briefly. 2.0% samples of naringin:Zinc complexes or Naringin starting material were prepared in 100% DMSO (BDH, cat#BDH 1115-1LP). Samples were then subjected to a 1:1 serial dilution in a 96 well clear flat bottom plate such that the highest concentration was 1.0% and the lowest concentration 0.0078% in 100 ul of DMSO. Samples were subjected to spectra scan from 200 nm wavelength to 500 nm wavelength. Plots of optical density (OD) vs wavelength for all serial dilutions were determined but only the results from 0.03125% dilution were presented in the Results section.

Figure 2:
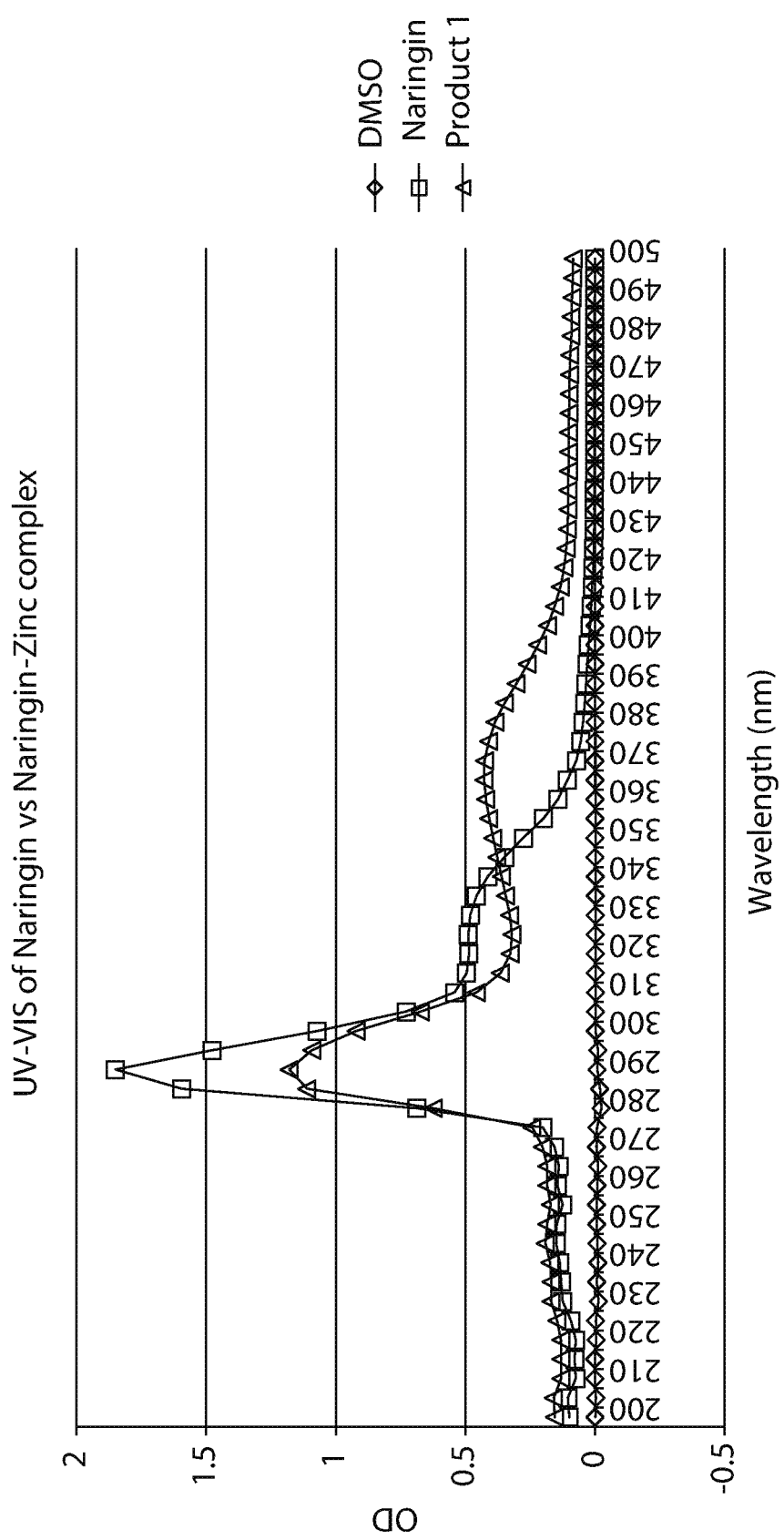
FIG. 2 is a UV-VIS spectrum of naringin compared to a 2:1 naringin:Zinc complex, Product 1, of the invention.
Figure 3:
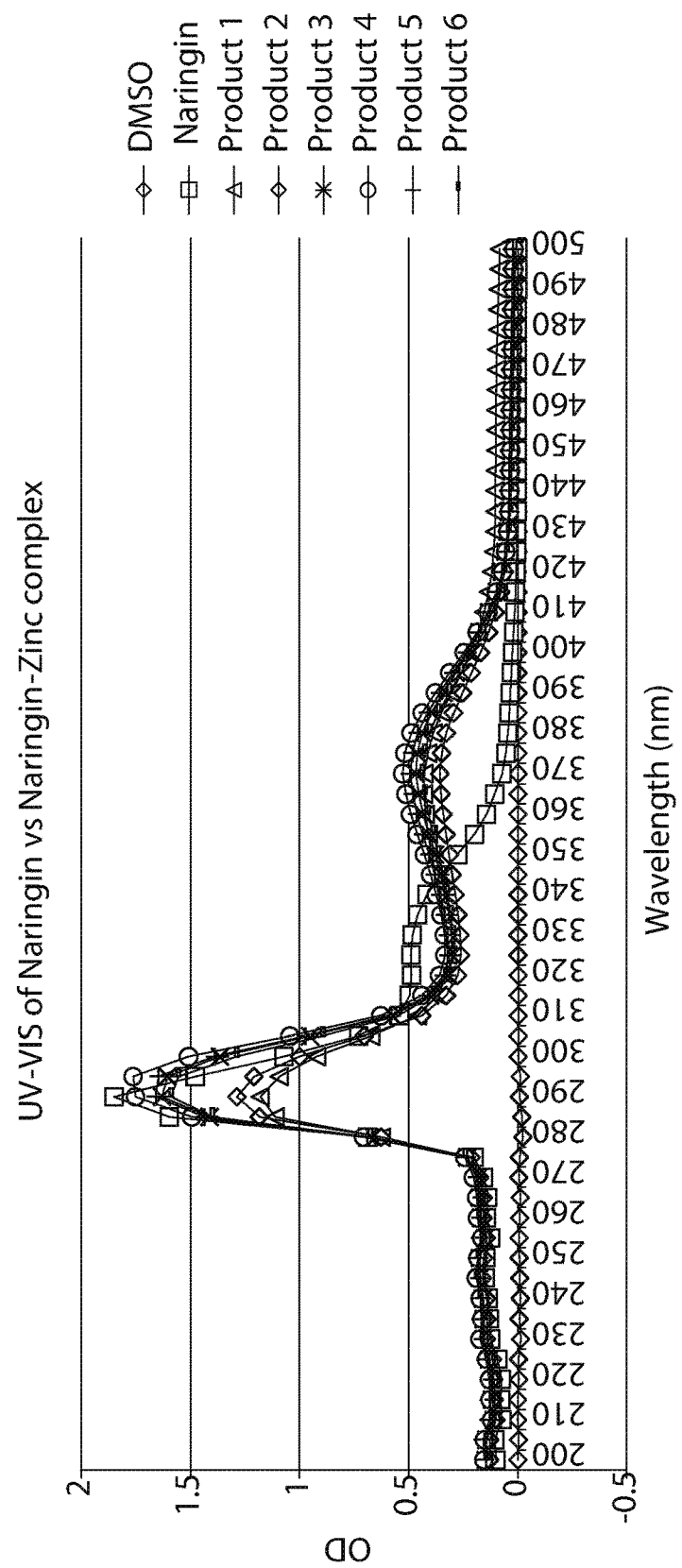
FIG. 3 is a UV-VIS spectrum of naringin compared to various 2:1 naringin:Zinc complex products, Products 1-6, of the invention.
Figure 4:
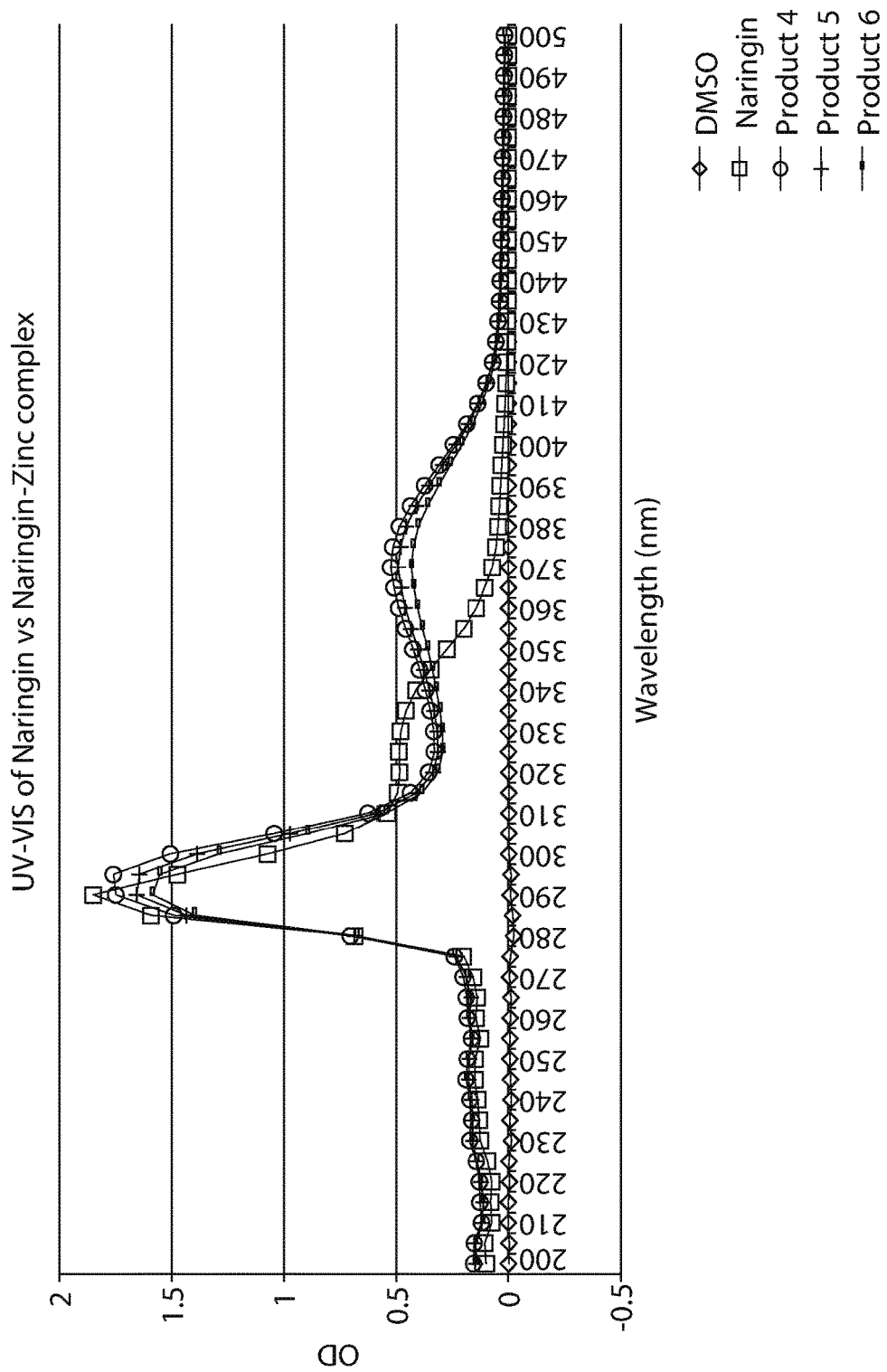
FIG. 4 is a UV-VIS spectrum of naringin compared to various 2:1 naringin:Zinc complex products, Products 4-6, of the invention.

As shown in FIGS. 2-4, free Naringin exhibits an absorption maximum peak in aqueous solution at 290 nm, corresponding to the A ring absorption (benzoyl system), and a weaker band at 325 nm, corresponding to the B ring absorption (cinnamoyl system) see Malesev et al., *J. Serb. Chem. Soc.*, 2007, 72(10): 921-39. Upon binding with Zinc Acetate to form the complex, a shift in the weaker absorption band from 325 nm to 365 nm was noted for Product 1. As shown in FIG. 3, Product 2 produced a subtle shift at the maximum peak from 290 nm to 295 nm. A more dramatic shift was also observed for the weaker band from 325 nm to 370 nm. Product 3 provided a similar profile. As shown in FIG. 4, Products 4 and 5 both exhibited similar profiles. A shift in the maximal peak (290 nm to 295 nm) and the weaker band (325 nm to 370 nm) was observed suggesting an interaction of the Zinc (II) ion with the condensed ring of the flavanone. The shift was previously attributed to an increased conjugative effect resulting from new ring formation upon metal complexation (Malesev et al., supra). This result is consistent with the findings from FTIR and $^1$H-NMR studies (see FIG. 5—FIG. 7B). The maximal peak shift was seen on most occasions for the various products tested, but not during every test. See, for example, Product 1 compared to Product 2 in Table 1.

TABLE 1

Summary showing the peak position in A-ring absorption
and B-ring absorption for free Naringin and naringin:Zinc
complexes synthesized under various conditions.

| Samples | Maximal Peak | Weaker Band |
| --- | --- | --- |
| Naringin (free) | 290 nm | 325 nm |
| Product 1 | 290 nm | 365 nm |
| Product 2 | 295 nm | 370 nm |
| Product 3 | 295 nm | 370 nm |
| Product 4 | 295 nm | 370 nm |
| Product 5 | 295 nm | 370 nm |

Example 7—Characterization with FTIR

Infrared spectra were collected using a Bruker Vertex 70 FTIR spectrometer equipped with a GladiATR diamond ATR accessory (Pike technologies, Madison, Wis.). The spectral range was 80-4000 $cm^{-1}$ and a resolution of 4 $cm^{-1}$ was used. All measurements were carried out on powdered samples at room temperature.

Figure 5:
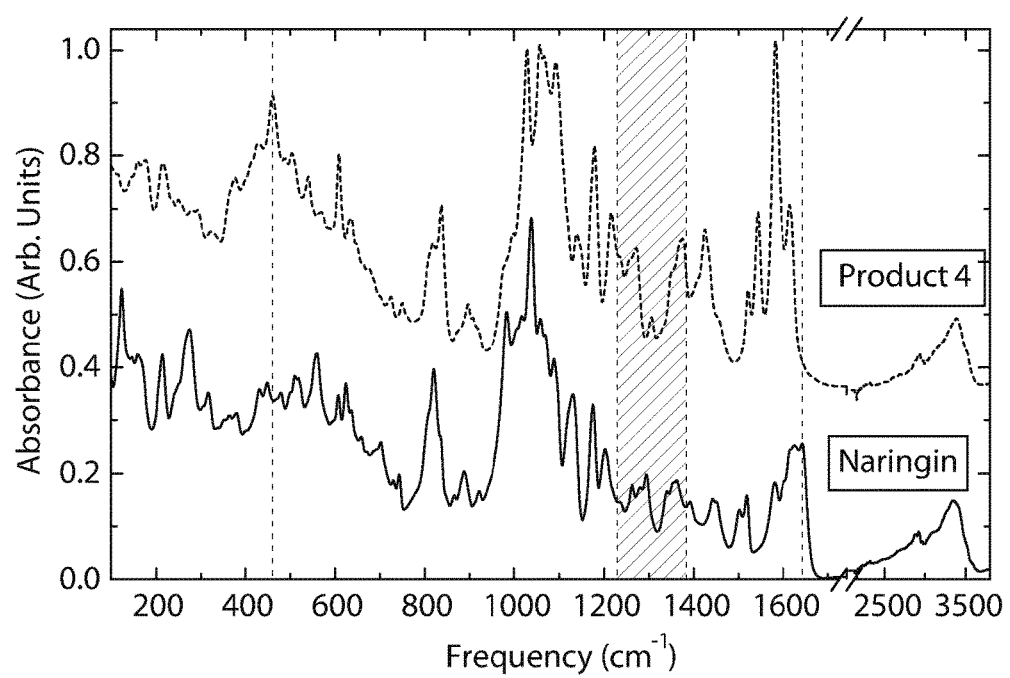
FIG. 5 is an infrared spectrum of naringin compared with 2:1 naringin:Zinc complex, Product 4. The spectra are offset for clarity. Dashed lines are used to bring focus towards differences in that range.

FIG. 5 displays the infrared spectra of free Naringin and Product 4 complex. The comparison of spectral data reveals pronounced differences in the vibrational response of Naringin upon interaction with Zinc. As an example, the infrared spectrum of Naringin exhibits a strong band near 1645 $cm^{-1}$ which is assigned to the stretching vibration of the carbonyl group $\nu(C=O)$ (Pereira et al., Molecules, 2007, 12: 1352-66; Li et al., Spectrochimica Acta Part A, 2007, 67:395-401; Yousuf et al., International Journal of Spectroscopy, 2014, Article ID 562160). In the presence of Zinc this band is red-shifted to 1615 $cm^{-1}$ suggesting coordination of Naringin to Zinc via the carbonyl oxygen. Similar behavior has been previously observed for other metal-flavonoid complexes (Pereira et al., Li et al., Yousuf et al., supra). In addition to the carbonyl moiety, the 5-OH group was found to be another important site for metal chelation in 5-hydroxyflavone derivatives. For the Product 4 complex, bands associated with $\nu(C—O(H))$ (or C—C—O) stretching vibrations of phenolic group are coupled with $\delta(OH)$ deformation modes and occur in the 1230-1370 $cm^{-1}$ range. As can be seen from FIG. 5, these bands display pronounced frequency shifts and relative intensity changes in comparison with the free naringin. This behavior together with the energy shift of the $\nu(C=O)$ band at 1645 $cm^{-1}$, suggest that zinc complexation with naringin likely takes place through the oxygen of the carbonyl group and the 5-hydroxyl group. Additional peak shifts and intensity variations in the bands of aromatic and dissacharide units of Product 4 may arise from the redistribution of electrons on the rings, as a result of a new ring formation, and conformational changes in glucoside, respectively. Finally, an additional band observed near 460 $cm^{-1}$ in complex Product 4 may originate from the $\nu$ (Zn—O) stretching vibration (Yousuf et al., supra) further supporting naringin:Zinc complexation.

Figure 6:
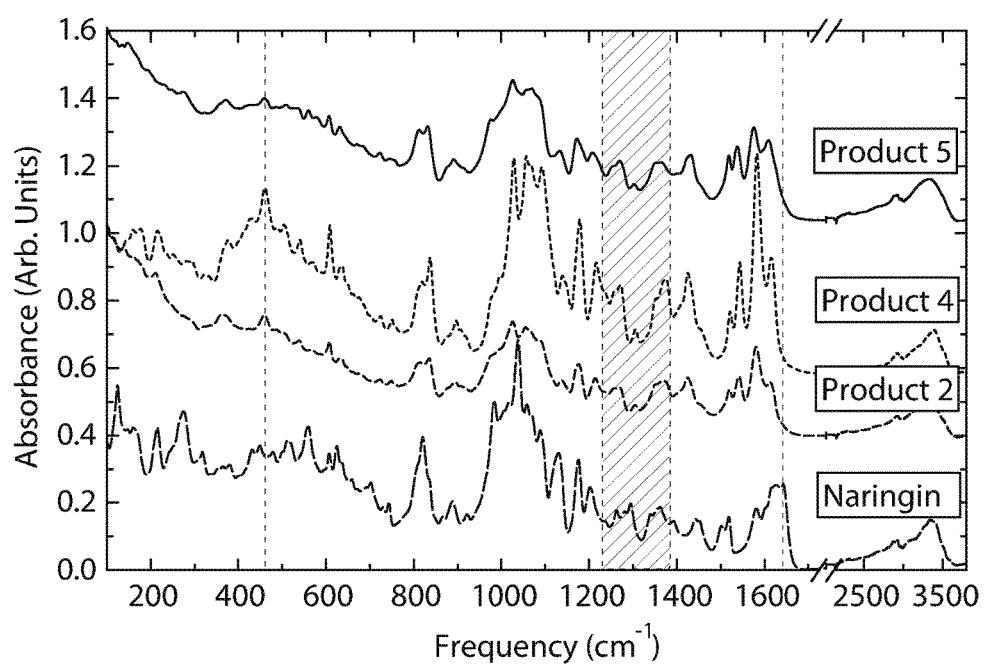
FIG. 6 is a comparison of the infrared vibrational spectra for naringin and complexes of Product 2, Product 4 and Product 5. The spectra are offset for clarity.

FIG. 6 compares the infrared response of naringin and naringin:zinc complexes of Product 2, Product 4 and Product 5, which were prepared under different pH and molar ratio conditions. Aside from differences in their relative intensities, all compounds show an overall similar spectral profile and peak shifts suggesting their similar structural features.

Example 8—Characterization with $^1$H NMR

The NMR measurements were performed on 10 wt % Naringin or naringin:Zinc samples in DMSO-d5 solutions. All $^1$H NMR spectra were acquired on a Bruker Avance 500 spectrometer working at 500 MHz for $^1$H at room temperature. Diffusion coefficients of the naringin and naringin:Zn complexes in DMSO-d5 were measured by $^1$H Pulse-field gradient NMR spectroscopy at 25° C. All chemical shifts were reported in $\delta$ (ppm) using TMS as the internal standard.

Figure 7A:
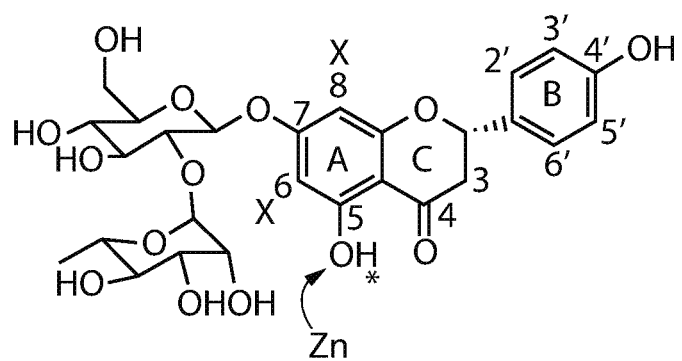
FIG. 7A shows a schematic of the Zinc ion coordinating with the hydroxyl group on the C5 of naringin.
Figure 7B:
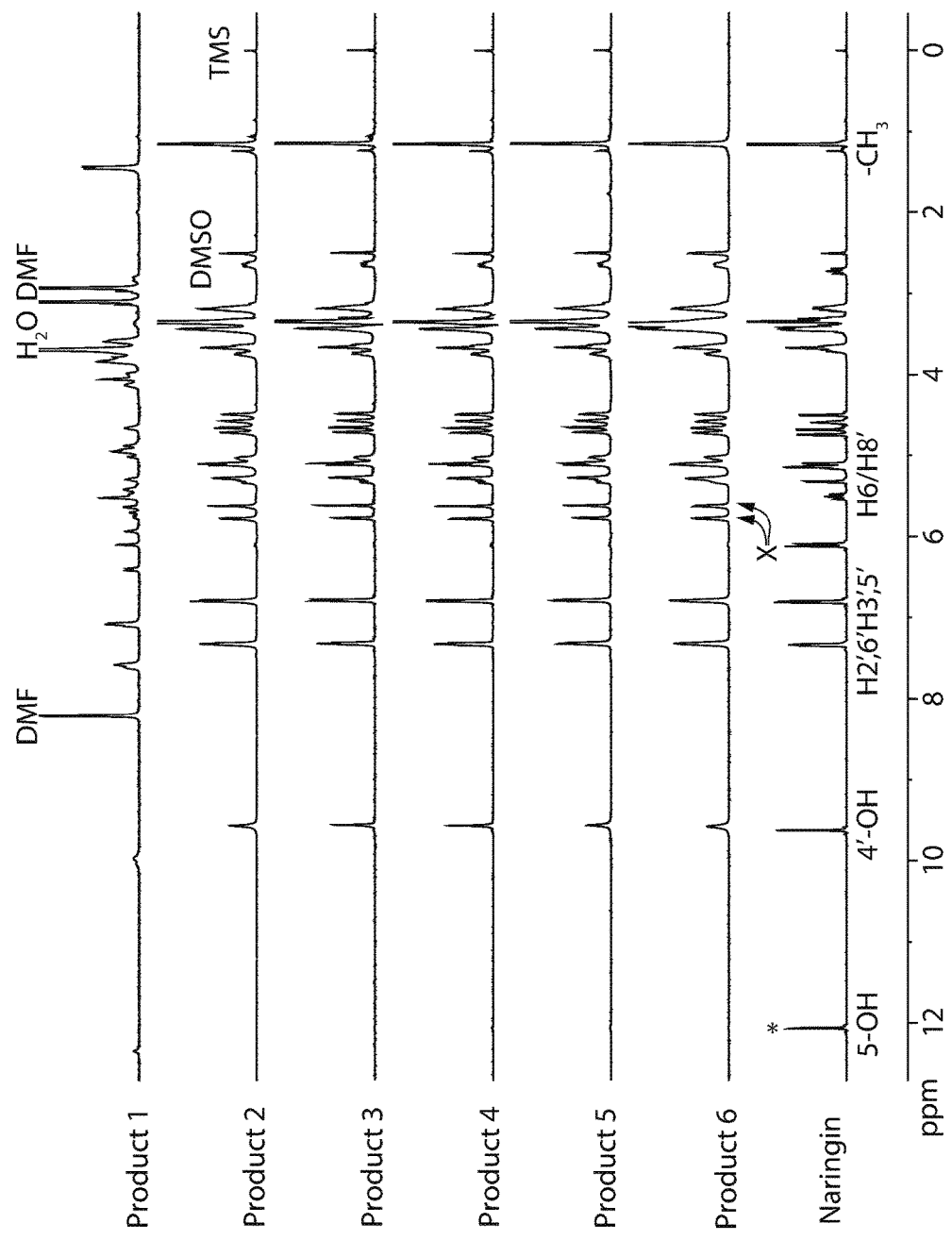
FIG. 7B is a $^1$H NMR spectra of naringin and 2:1 naringin:Zn complexes (Products 1-6) in DMSO-d5. The chemical shift values reported were referred to TMS as zero. Upper inlet shows proposed structural nomenclature of the 2:1 naringin:Zn complex.

The $^1$H chemical shifts for Naringin and naringin:Zinc complexes are presented in FIG. 7B and Table 2. Notably, the peak at 12 ppm corresponding to 5-OH phenolic group is absent upon naringin:Zinc complex formation, suggesting that this site conjugates with Zinc. The peaks assigned to be H6 and H8 of the A ring shift to lower frequency when forming complex. Without being bound to theory, this could be because the coordination increases the planarity of the flavonoid molecules and/or because coordination induces the large conformational change of the disaccharide, thereby increasing the electron densities on the ring A to shield proton H6 and H8.

TABLE 2

$^1$H NMR chemical shifts (ppm) for Naringin
and Naringin:Zinc complexes.

| Sample | Naringin | Product 4 | Product 5 |
| --- | --- | --- | --- |
| Naringin:Zn | | 1:1 | 2:1 |
| 5-OH | 12.07 | | |
| 4'-OH | 9.62 | 9.56 | 9.57 |
| H2', H6' | 7.34 (d, J = 8 Hz) | 7.31 (d, J = 8 Hz) | 7.31 (d, J = 8 Hz) |
| H3', H5' | 6.80 (d, J = 8 Hz) | 6.79 (d, J = 8 Hz) | 6.78 (d, J = 8 Hz) |
| H8 | 6.18 | 5.63 | 5.63 |
| H6 | 6.22 | 5.78 | 5.79 |
| H3 | 3.17 | 3.20 | 3.18 |

Surprisingly, the $^1$H NMR spectra as well as the FTIR spectra show that the naringin:zinc complex samples prepared from different ratios of naringin and zinc (2:1 or 1:1) were similar.

Example 9—Characterization with Diffusion Measurements

Diffusion measurements were performed using Bruker Avance 500 spectrometer equipped with an observed broadband probe with a z axis gradient coil with maximum gradient strength of 72 G/cm. A double stimulated echo pulse sequence with bipolar gradient pulses and two spoil gradients were used. The diffusion time was 0.1 second. The duration of the field gradient pulse was adjusted to be 4 milliseconds. The pulse gradients were incremented from 5 to 95% of the maximum gradient strength in a linear ramp with a total of experimental time of 45 minutes.

Figure 8:
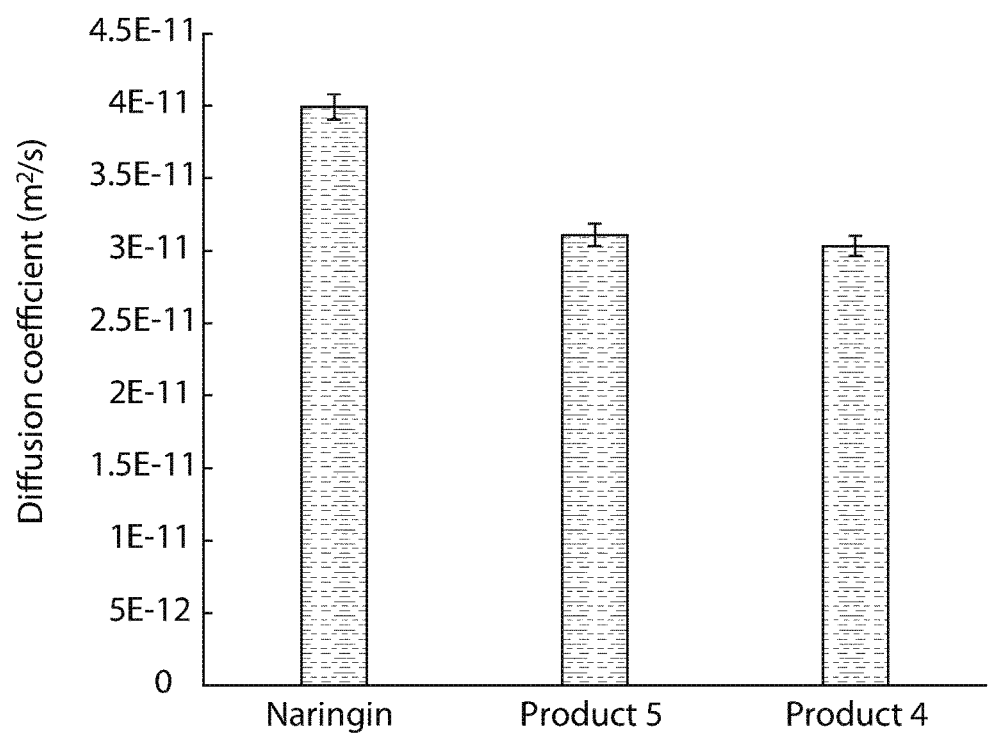
FIG. 8 is a bar graph showing the experimentally derived diffusion coefficient of naringin and 2:1 naringin:Zinc complexes (Product 4 and Product 5) in DMSO-d5.

The molecular diffusion of Naringin:Zinc complex was performed to detect differences between samples prepared from 2:1 versus 1:1 Naringin:Zinc molar ratios. Without being bound to theory, it was postulated that molecular diffusion of a 2:1 should be slower than a 1:1 complex. The observed diffusion coefficients of the Naringin and Naringin:Zinc complexes of Product 4 and Product 5 are summarized in FIG. 8. The diffusion coefficients of the complexes are about 25% slower than that of Naringin. It was also observed that the diffusion coefficients for all two Naringin:Zinc complexes tested were similar, regardless whether they were prepared from the initial mixing of 1:1 or 2:1 Naringin:Zinc molar ratios. These findings imply that both Naringin:Zinc complexes have the same stoichiometric ratio of Naringin and Zinc.

The calculated diffusion coefficient was used to elucidate the size of the molecular species using the Stokes-Einstein relation:

$$D = \frac{k_B T}{6\pi\eta r}$$

where r is the hydrodynamic radius of a hard sphere moving in a continuum fluid of viscosity η at temperature T and $k_B$ is the Boltzmann constant. Assuming the diffusing species to be spherical, the relation of D and molecular weight MW can be described as $$D = \frac{k_B T}{6\pi\eta} \sqrt[3]{\frac{4\pi\rho N_A}{3MW}}$$

where ρ is the effective molecular density of the molecule and $N_A$ is Avogadro's number. Assuming the Naringin and Naringin:Zinc complexes studied herein have the same packing effect and geometry, the molecular weight of Naringin:Zinc complex can be estimated according to the known molecular weight of Naringin and diffusion coefficient D according to the relationship:

$$MW \propto 1/D^3$$

TABLE 3

Summary of the estimated molecular weight and stoichiometric ratio of Naringin to Zinc based on diffusion NMR measurement.

| Sample | Diffusion coefficient (×10⁻¹¹ m²/s) | Estimated molecular weight (mol/g) | Estimated stoichiometric ratio of Naringin to Zinc |
|---|---|---|---|
| Naringin | 3.99 ± 0.09 | 580.54 | — |
| Product 5 | 3.11 ± 0.08 | 1228.4 | 2.1:1 |
| Product 4 | 2.99 ± 0.08 | 1376.3 | 2.4:1 |

From Table 3, the estimated stoichiometric ratio of Naringin and Zinc based upon the estimated molecular weight was found to be approximately 2:1 (Naringin:Zinc).

Example 10—Characterization of Melting Point

Melting points were recorded on an Electrothermal MEL-TEMP 3.0 (Barnstead International, Dubuque, Iowa) melting point apparatus. Small amounts of the samples were introduced into the capillary tube. The tube was inserted into the holder and the samples were monitored from the observation window for physical changes. Temperatures were recorded when changes occurred. Melting points for the samples are summarized in Table 4. All samples showed disintegration in the range of 230-254.3° C.

TABLE 4

Summary of the melting points for naringin and naringin:zinc complexes synthesized from methods described herein.

| Sample | Description | Test | Method | Result | Comments |
|---|---|---|---|---|---|
| 1 | Naringin | melting point/range | USP/EP | 165.5-168.1 | turns light brown |
| 2 | Product 1 | melting point/range | USP/EP | No melting observed up to 380.9° C. | color change observed: @239.7° C. turned brown |
| 3 | Product 2 | melting point/range | USP/EP | No melting observed up to 380.9° C. | @230.0° C.-turned brown, @ 232.1° C. black hue notice in tube on top of sample. @254.3° C. sample turned black. |
| 4 | Product 3 | melting point/range | USP/EP | No melting observed up to 380.9° C. | @226.3° C. turned brown. Shortly after a black hue was notice in tube on top of sample. @248.4° C. sample turned black. |
| 5 | Product 4 | melting point/range | USP/EP | no melting observed | 234.6° C. turned dark brown and started to shrink into a ball but did not liquify. By 239.4° C. a little bubbling was noticed and eventually started to darken in color. |
| 6 | Product 5 | melting point/range | USP/EP | No melting observed up to 380.9° C. | @221.7° C. turned amber in color. @228.6° C. the sample seemed to have "shrunk" or had contracted into a round-like form. @230.0° C. sample expanded upwards in the tube. Black hue was noticed in tube on top of sample. @254.3° C. sample turned black. |
| 7 | Product 6 | melting point/range | USP/EP | No melting observed up to 250.0° C. | Sample turned from yellow (initial color) to dark orange @ 225.1° C. Sample turned dark brown and it's physical form looked more compacted (shrunk in size) @ 228.0° C. Compacted sample darkened until practically black in color up to 250.0° C. |

Example 11—Stability Characterization

Figure 9:
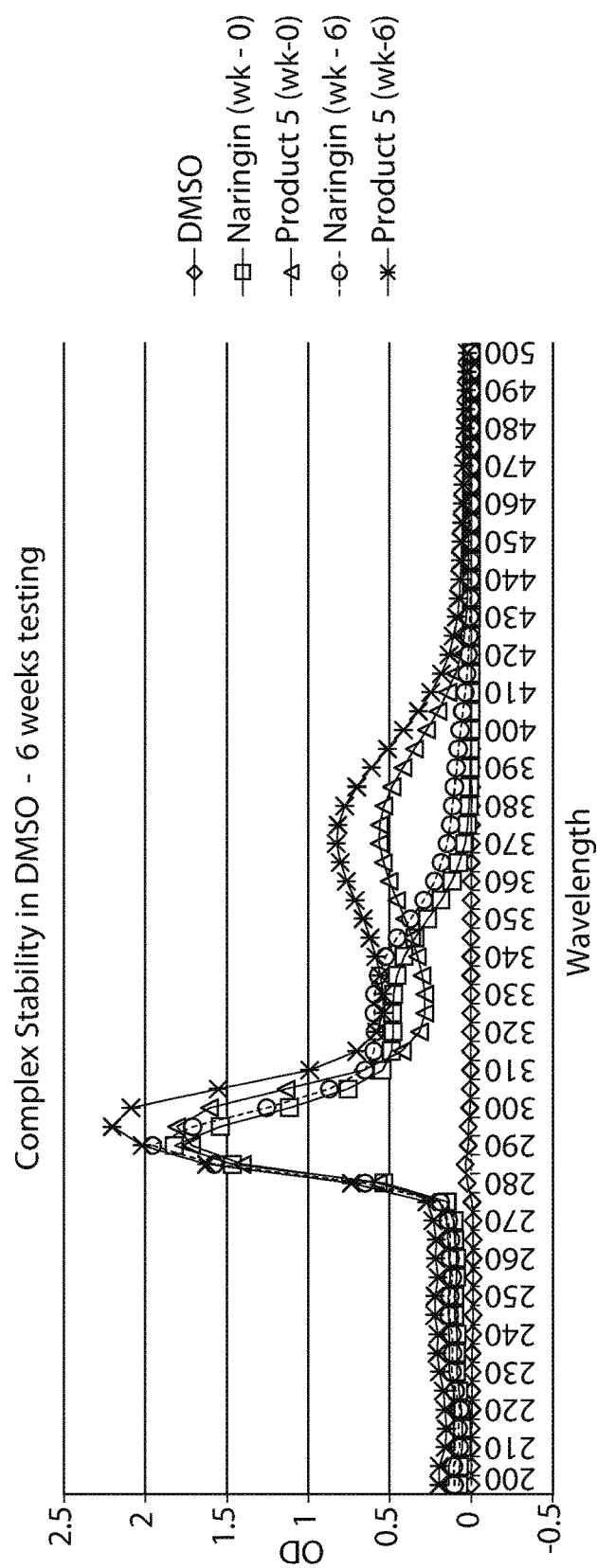
FIG. 9 is a UV-Vis spectra comparison of naringin and 2:1 naringin:Zinc complex, Product 5, at week 0 and at week 6.
Figure 10:
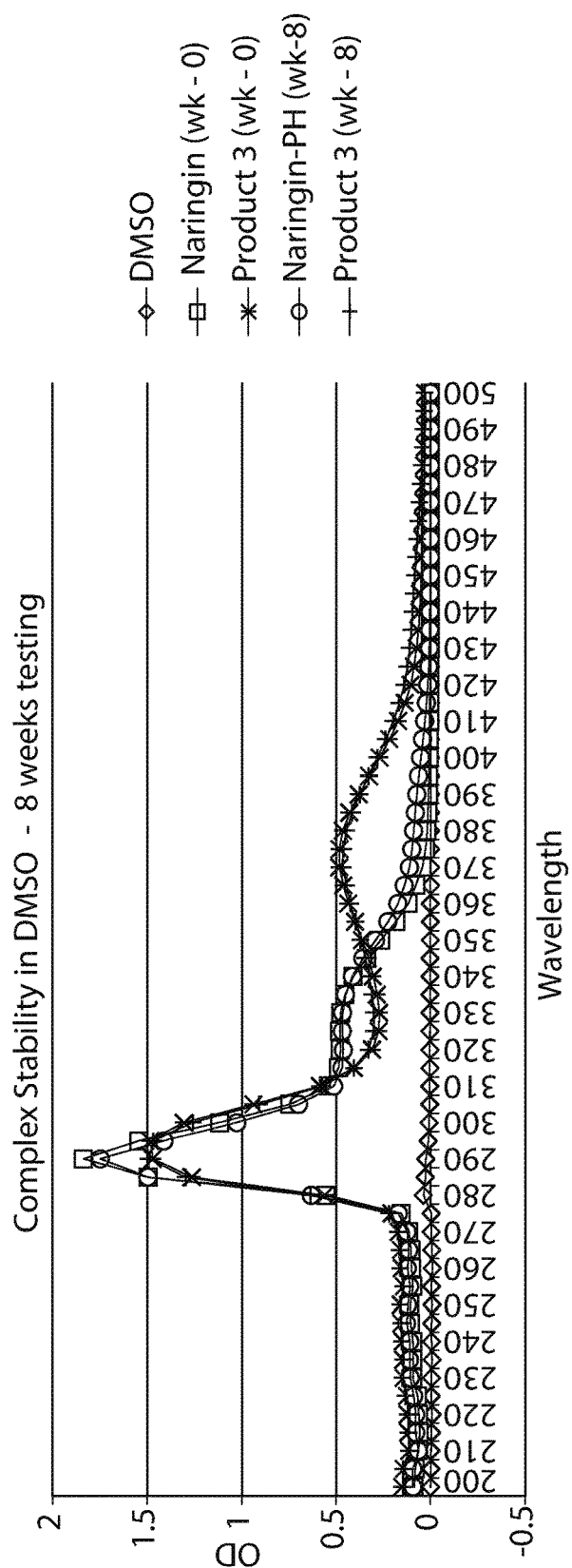
FIG. 10 is a UV-Vis spectra comparison of naringin and 2:1 naringin:Zinc Complex, Product 3, at week 0 and at week 8.

To initiate stability testing of the complex, selective samples were dissolved in DMSO at 2% stock solution for initial UV—Visual spectra and allowed to sit for 6-8 weeks at room temperature. Samples were subjected to 1:1 serial dilutions in DMSO and read using the SpectraMax M5 Plate Reader. Results are summarized in FIG. 9 and FIG. 10. The shifts observed previously for the maximal peak (290 nm to 295 nm) and the weaker band (325 nm to 370 nm) were maintained 6-8 weeks post sample preparation.

Example 12—Characterization of Antimicrobial Activity: Zone of Inhibition

Antimicrobial activity was determined using a zone of inhibition type analysis in combination with growth inhibition/toxicity testing. For zone of inhibition determination, a single colony of *Aggregatibacter actinomycetemcomitans* (A.a) was cultured in approximately 30 ml of BHI broth (BD, cat #237500) supplemented with 0.5% Yeast Extract (BD, cat #210941) in 37° C. and 5% $CO_2$ overnight. A 1:10 dilution of the overnight culture at ($OD_{610}$ 0.5) was prepared and a 100 µl culture was aseptically transferred onto room temperature equilibrated TSAII (Trypticase soy agar with 5% sheep blood) plates (BD, cat #221239) and gently spread out using a sterile spreader. A sterile 6 mm diameter filter disc was place on top of the cultured plate using sterile forceps and 5 µl of a 100 mM test compound in DMSO was applied to the center of the filter disc along with the appropriate controls 1% chlorohexidine (CHX), 3% Triclosan, media only and DMSO. Treated plates were incubated in 37° C., 5% $CO_2$ for 48 hours prior to observations and diameter of zone of inhibition being measured. Table 5 summarizes the activity of the naringin:Zinc complex on the oral pathogen A.a.

TABLE 5

Antimicrobial effects of free Naringin vs. Naringin:Zinc complexes represented by the formation of zone of inhibition around filter discs.

| Samples (@ 500 nmoles) | Zone of Inhibition in duplicates (diameter including the disc itself) against *Aggregatibacter actinomycetemcomitans* | |
|---|---|---|
| | # 1 (cm) | # 2 (cm) |
| Naringin alone | 0.6 × 0.6 (size of filter disc) | 0.6 × 0.6 (size of filter disc) |
| Product 1 | 1.5 × 1.5 | 1.8 × 1.5 |
| Product 2 | 1.8 × 1.4 | 1.9 × 1.8 |
| Product 3 | 1.1 × 1.2 | 1.2 × 1.4 |
| Product 4 | 1.5 × 1.2 | 1.5 × 1.3 |
| Product 5 | ND | ND |

The zone of inhibition method yields qualitative results regarding the antimicrobial activity of the complexes. Appearance of zone of inhibition around the disc is an indicative of antimicrobial activity of the test compound spotted onto the filter disc. The oral pathogen *A. actinomycetemcomitans* was chosen here because it is regarded as a key bacterial agent associated with aggressive periodontitis in young adults and is implicated in adult forms of destructive periodontal disease (Darby et al., *Periodontology* 2000, 2001, 26:33-53). Data from the zone of inhibition studies indicated that at 500 nmoles, the Naringin:Zinc complex showed an increased potency in killing A.a compared to Naringin alone. DMSO alone did not show any killing while 1% Chlorohexidine did.

Example 13—Characterization of Antimicrobial Activity: Growth Inhibition/$IC_{50}$ Determination Single species of *Streptococcus gordonii* (*S. gordonii*, S.g) strain V288 (ATCC #35105), *Streptococcus sobrinus* (*S. sobrinus*, S.s) strain SL1 [CCM 6070, CNCTC 9/89] (ATCC #33478), or *Aggregatibacter actinomycetemcomitans* were analyzed. Also, a mixed culture containing *Actinomyces viscosus* (*A. viscosus*, A.v) strain (ATCC, #43146), *Lactobacillus casei* (*L. casei*, L.c) strain (ATCC #334), *Streptococcus oralis* (*S. oralis*, S.o) strain (ATCC #35037), *Fusobacterium nucleatum* (*F. nucleatum*, F. n) strain (ATCC #10953), and *Veilonella parvula* (*V. parvula*, V. p) strain (ATCC #17745) was also analyzed for growth inhibition/toxicity activity. Bacteria were cultured overnight in approximately 20 ml of BHI broth (BD, cat #237500) or maintained in a specialized complex modified BHI II medium in a continuous culture chemostat at 37° C. respectively. The following day, the $OD_{610}$ were determined and solutions diluted to an $OD_{610}$ of 0.2 or 0.1 respectively for the assay.

Figure 11:
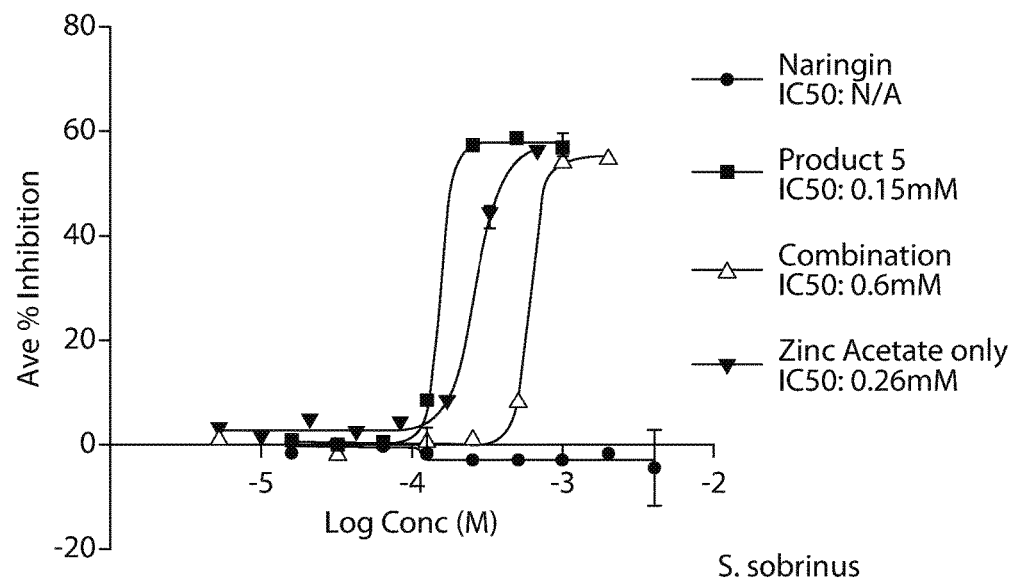
FIG. 11 is a dose response curve comparison of 2:1 naringin:Zinc complex (Product 5), naringin+Zinc acetate combination, Zinc Acetate alone and naringin alone for *Streptococcus sobrinus*.
Figure 12:
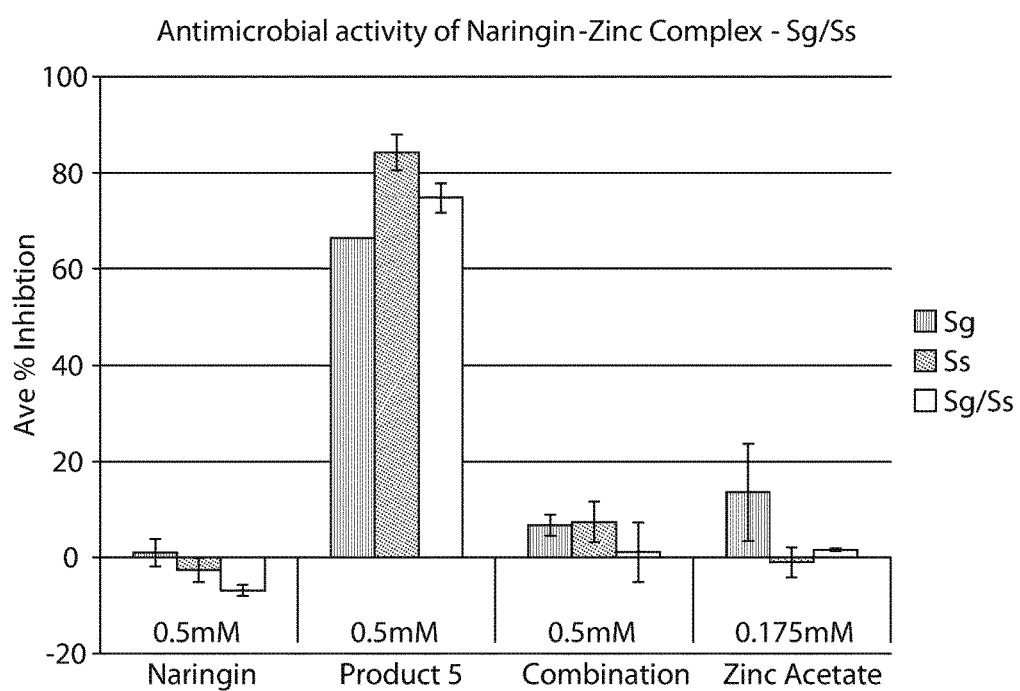
FIG. 12 shows the antimicrobial activity of naringin alone, 2:1 naringin:Zinc complex (Product 5), naringin+ Zinc acetate combination, and Zinc Acetate alone on single cultures of *S. gordonii* (S.g), *S. sobrinus* (S.s) or as co-cultures of *S. gordonii* and *S. sobrinus*.
Figure 13:
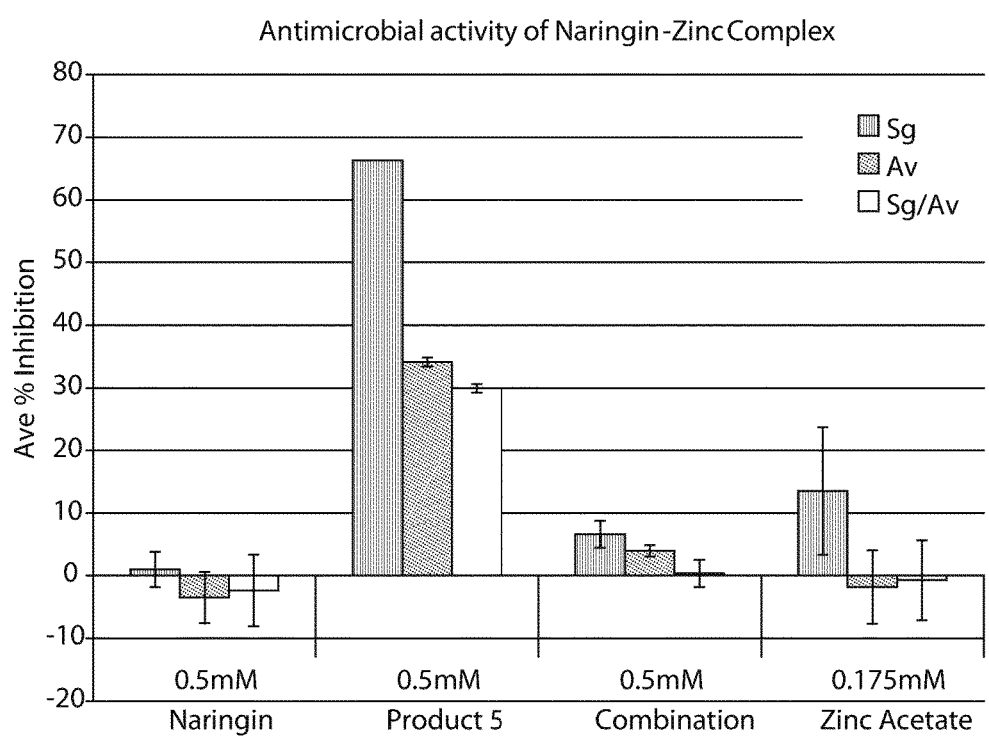
FIG. 13 shows the antimicrobial activity of naringin alone, 2:1 naringin:Zinc complex (Product 5), naringin+ Zinc acetate combination, and Zinc Acetate alone on single cultures of *S. gordonii* (S.g), *A. viscosus* (A.v) or as co-cultures of *S. gordonii* and *A. viscosus*.
Figure 14:
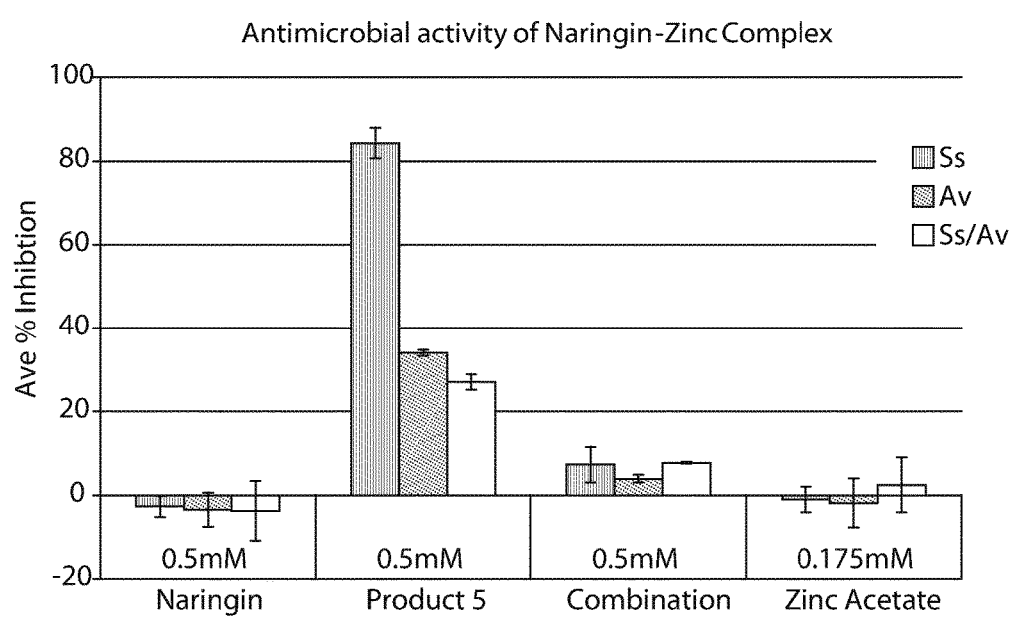
FIG. 14 shows the antimicrobial activity of naringin alone, 2:1 naringin:Zinc complex (Product 5), naringin+ Zinc acetate combination, and Zinc Acetate alone on single cultures of *S. sobrinus* (S.s), *A. viscosus* (A.v) or as co-cultures of *S. sobrinus* and *A. viscosus*.
Figure 15:
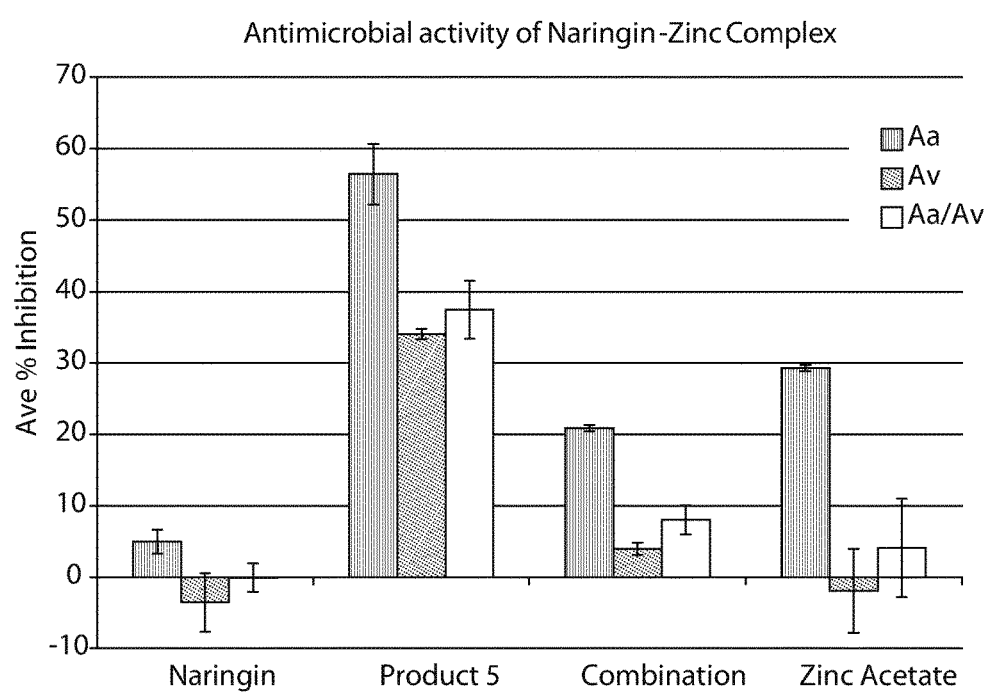
FIG. 15 shows the antimicrobial activity of naringin alone, 2:1 naringin:Zinc complex (Product 5), naringin+ Zinc acetate combination, and Zinc Acetate alone on single cultures of *A. actinomycetemcomitans* (A.a), *A. viscosus* (A.v) or as co-cultures of *A. actinomycetemcomitans* and *A. viscosus*.
Figure 16:
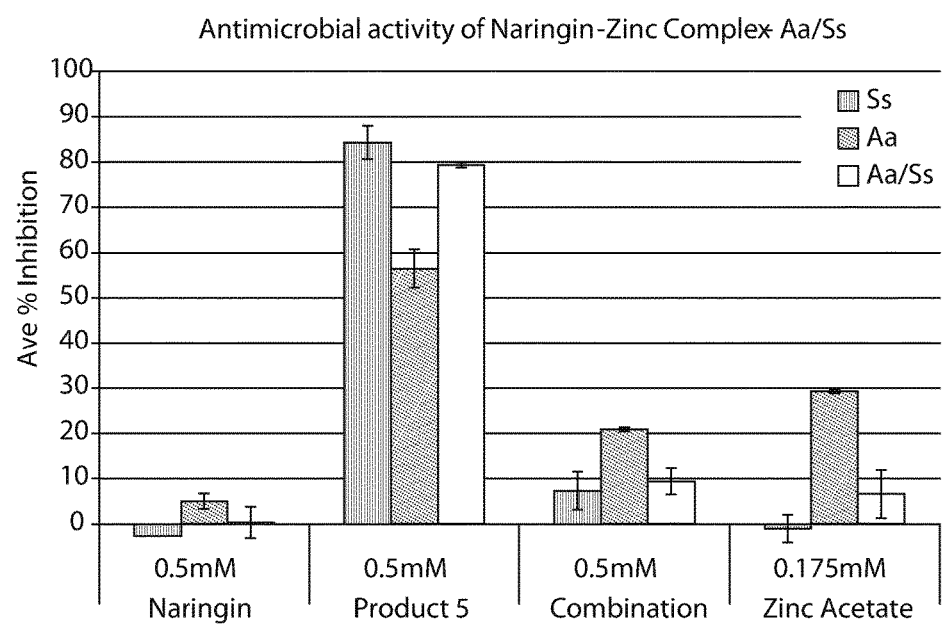
FIG. 16 shows the antimicrobial activity of naringin alone, 2:1 naringin:Zinc complex (Product 5), naringin+ Zinc acetate combination, and Zinc Acetate alone on single cultures of *S. sobrinus* (S.s) and *A. actinomycetemcomitans* (A.a) or as co-cultures of *S. sobrinus* and *A. actinomycetemcomitans*.

Test samples (naringin, naringin:Zinc complex and naringin+Zinc acetate combination) were prepared as a 200 mM stock solution followed by 2 fold serial dilutions in 100% DMSO. Triclosan (positive control) was prepared as a 10% stock in 100% EtOH and 3 fold serial dilutions were performed in 100% EtOH. An appropriate amount of the diluted samples was then transferred into a 96 well clear plate such that the resulting final concentration of the test samples ranged from either a 2 mM or 4 mM (highest concentration) to 0.0078 mM or 0.0156 mM (lowest concentration respectively) in 2% DMSO in 100 µl media per well. Triclosan (TCN) ranged from 0.01% to 1.67e-6% in 1% EtOH. For Zinc acetate, in order to mimic the 2:1 molar ratio (ligand:Zinc) in the Naringin:Zinc complex, the final concentration ranged from 0.7 mM to 0.0027 mM for samples with 2 mM as the highest concentration and 1.33 mM to 0.052 mM for samples with 4 mM as the highest concentration in 2% DMSO. Next, 100l of bacterial culture at $OD_{610}$ 0.2 were introduced to the wells with the test samples. The wells were thoroughly mixed and incubated at 37° C. overnight. The plates were read using an Envision plate reader (PerkinElmer, Waltham, Mass.) at 610 nm. Representative findings are summarized in FIG. 11.

Figure 22:
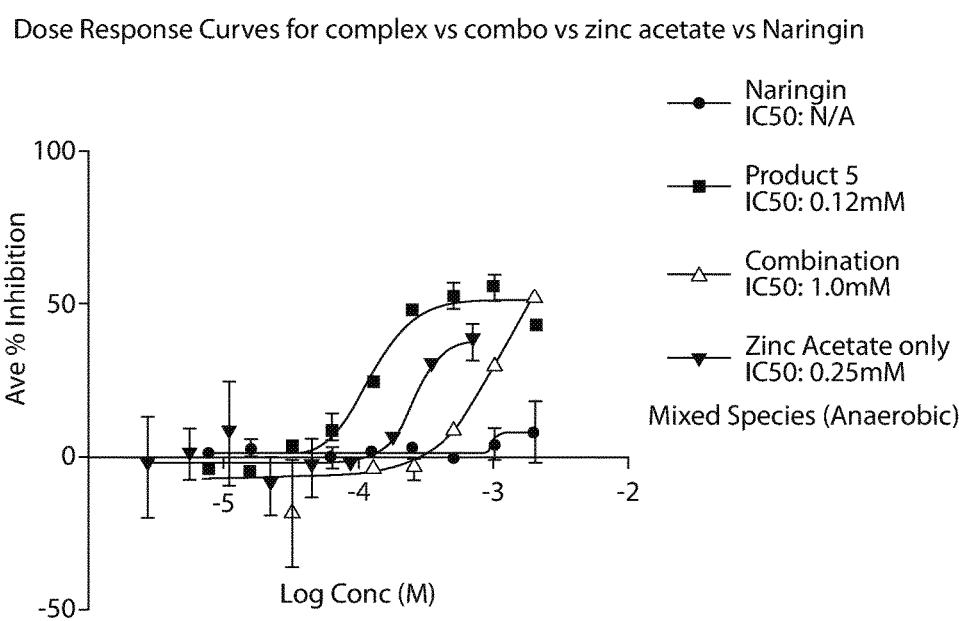
FIG. 22 is a dose response curve comparison of 2:1 naringin:Zinc complex (Product 5), naringin+Zinc acetate combination, Zinc Acetate alone and naringin alone on a mixed culture grown under anaerobic conditions.

The $IC_{50}$ for the complex, Product 5, was determined for *Streptococcus gordonii* (*S. gordonii*), *Streptococcus sobrinus* (*S. sobrinus*), *Aggregatibacter actinomycetemcomitans* (*A. actinomycetemcomitans*), and also for the mixed bacterial culture. The dose response curves were plotted using GraphPad Prism 6 and representative plots are presented in FIGS. 11 and 22. Determined $IC_{50}$ values are summarized in Table 6. The $IC_{50}$ values show that the complex was more potent than both the Zinc Acetate alone as well as the combination of Naringin+Zinc Acetate taken together. Triclosan (TCN) was included as a positive control for bacterial inhibition.

TABLE 6

Summary of IC$_{50}$ values for single and mixed cultures.

| | IC 50 (mM) | | | | |
|---|---|---|---|---|---|
| Bacterial Strain | Naringin alone | Product 5 | Combination of Naringin/ Zinc Acetate (2:1) | Zinc Acetate alone | IC50 (mM) TCN |
| *Streptococcus sobrinus* | N/A | 0.22 ± 0.06 | 1.03 ± 0.57 | 0.29 ± 0.04 | 0.0060 ± 0.0017 |
| *Streptococcus gordonii* | N/A | 0.22 ± 0.07 | 1.1 ± 0.15 | 0.3 ± 0.02 | 0.0060 ± 0.00085 |
| *Aggregatibacter actinomycetemcomitans* | N/A | 0.37 ± 0.18 | 2.10 ± 0.28 | 1.73 ± 0.95 | 0.00061 ± 0.00046 |
| Mixed Species (aerobic) | N/A | 0.1 | 0.67 | Ambiguous | 0.0076 |
| Mixed Species (anaerobic) | N/A | 0.12 | 1.0 | 0.25 | 0.0048 |

The complex exhibited anti-microbial effects on cariogenic pathogen *S. sobinus*, commensal pathogen *S. gordonii* and pathogenic late colonizer oral microflora *A. actinomycetemcomitans*. These findings were extended to mixed chemostat bacterial cultures as well. The concentration that inhibited 50% of the bacterial growth ranged from 0.1-0.37 mM (corresponding to 122.6-453.5 ppm). Naringin in combination with Zinc Acetate generated IC$_{50}$ values ranging from 0.65-2.10 mM (corresponding to 496.5-1604.2 ppm). Naringin alone at all concentrations tested did not show detectable antimicrobial effect on bacterial species tested. Zinc Acetate alone exhibits an IC$_{50}$ ranging from 0.25-1.73 mM (corresponding to 45.9-317.5 ppm). The positive control Triclosan, inhibits 50% of both bacteria species in the range 0.00061-0.0076 mM (corresponding 0.18-2.2 ppm)

Further characterization was performed on planktonic oral microbes; *Streptococcus sobrinus* (Cariongenic—strain-SL1 [CCM 6070, CNCTC 9/89] (ATCC cat. #33478), *Streptococcus gordonii* (Arginolytic—strain V288 (ATCC cat. #35105), *Actinomyces viscosus*) as well late colonizer (Gram −), pathogenic *Aggregatibacter actinomycetemcomitans*. All microbes were grown in their respective culture media: *Streptococcus sobrinus* and *Streptococcus gordonii* in BHI broth (BD, cat #237500), *Aggregatibacter actinomycetemcomitans* in BHI broth supplemented with 0.5% Yeast Extract (BD, cat #210941) and *Actinomyces viscosus* in Trypticase Soy Broth (BD, cat #211768) supplemented with 0.5% Yeast Extract (BD, cat #210941). Bacteria were cultured overnight in 37° C., 5% CO$_2$ in approximately 20 ml of the appropriate culture broth. The following day, the OD$_{610}$ was determined and solutions were diluted to 0.2 for the assay.

Test samples (Naringin, Naringin:Zinc complex and Naringin+Zinc Acetate (combination)) were prepared as a 100 mM stock solution followed by 2 fold serial dilution in 100% DMSO. Triclosan (positive control) was prepared as a 10% stock in 100% EtOH and 3 fold serial dilutions were done in 100% EtOH. An appropriate amount of the diluted samples were transferred into 96 well clear plate such that the resulting final concentration of naringin alone, naringin:Zinc complexes, naringin+Zinc acetate (combination) ranged from 2 mM to 0.0078 mM (2% DMSO) and Triclosan ranged from 0.01% to 1.7e-6% (1% EtOH), in 100 ul media per well. For Naringin+Zinc combination, while the highest total overall concentration was 2 mM, the exact concentration was Naringin (1.3 mM) and Zinc Acetate (0.7 mM) due to the compositions 2:1 molar ratio. For Zinc Acetate, in order to mimic the 2:1 ratio (ligand:Zinc) composition as in the complex, the final concentration ranged from 0.7 mM to 0.0027 mM in 2% DMSO.

A 100 µl aliquot of bacterial culture at OD$_{610}$ 0.2 were introduced to the wells with the test samples. The wells were thoroughly mixed and plates incubated overnight in a 37° C. incubator with or without 5% CO$_2$ depending upon the bacterial species. Additionally, co-cultures of various bacterial species (S.s+A.a; A.a+A.v; S.s+A.v; S.g+A.v; S.g+S.s) were also performed. In such case, 50 µl of each bacterial culture was utilized for a total volume of 100 µl per well.

After approximately 12-13 hours of treatment, the plate was read at 610 nm using an Envision plate reader (PerkinElmer, Waltham, Mass.). The % inhibition relative to control was determined as follows:

$$\% \text{ Inhibition} = 100\% - \left(\frac{\text{Treated Sample}}{\text{Control}} \times 100\%\right)$$

Naringin:Zinc complex exhibits a synergistic antimicrobial effect on both Gram + and Gram − planktonic oral bacterial species, cultured alone or as co-cultures with another bacterial species. See FIGS. 11-18 and Tables 6-12.

TABLE 7

Effects of treatments on the % inhibition of *S. gordonii* and *S. sobrinus*. The concentration of sample treatment chosen to mimic the stoichiometric ratio of 2:1 (Naringin to Zinc).

| | % Inhibition | | | |
|---|---|---|---|---|
| Bacterial species | Naringin alone (0.5 mM) | Naringin:Zinc Complex (0.5 mM) | Naringin (0.325 mM) + Zinc acetate (0.175 mM) (0.5 mM total) | Zinc Acetate alone (0.175 mM) |
| *S. gordonii* | 0.96 ± 2.82 | 66.35 ± 0.00 | 6.62 ± 2.17 | 13.51 ± 10.18 |
| *S. sobrinus* | −2.64 ± 2.54 | 84.30 ± 3.67 | 7.33 ± 4.23 | −1.05 ± 3.10 |
| *S. gordonii/ S. sobrinus* | −6.84 ± 1.19 | 74.8 ± 3.09 | 1.05 ± 6.17 | 1.55 ± 0.24 |

The Naringin-Zinc complex when added to single or co-cultured bacterium resulted in a synergistic inhibition of both single species and of co-cultures of bacteria. Naringin alone, in combination with Zinc acetate or Zinc acetate alone showed little to no detectable inhibition. Additionally, the complex appeared to exhibit differential effects on different species of bacteria. In this case, the complex at 0.5 mM is more effective as an antimicrobial agent against *S. sobrinus* (84.30%) than *S. gordonii* (66.35%) and co-cultures of both resulted in 74.8% inhibition.

TABLE 8

Effects of treatments on the % inhibition of S. gordonii and S. sobrinus. The concentration of the sample treatment was chosen to mimic the stoichiometric ratio of 2:1 (Naringin to Zinc).

| Bacterial species | % Inhibition | | | |
|---|---|---|---|---|
| | Naringin alone (0.5 mM) | Naringin:Zinc Complex (0.5 mM) | Naringin (0.325 mM) + Zinc acetate (0.175 mM) (0.5 mM total) | Zinc Acetate alone (0.175 mM) |
| S. gordonii | 0.96 ± 2.82 | 66.35 ± 0.00 | 6.62 ± 2.17 | 13.51 ± 10.18 |
| A. viscosus | −3.50 ± 4.10 | 34.13 ± 0.73 | 3.96 ± 0.88 | −1.84 ± 5.86 |
| S. gordonii/ A. viscosus | −2.39 ± 5.68 | 29.9 ± 0.67 | 0.32 ± 2.17 | −0.74 ± 6.34 |

The naringin:Zinc complex when added to single or co-cultured bacterium resulted in a synergistic inhibition of both single species and of co-cultures of bacteria. Naringin alone, in combination with Zinc Acetate or Zinc Acetate alone showed little to no detectable inhibition. Additionally, the complex appeared to exhibit differential effects on different species of bacteria. In this case, the complex at 0.5 mM is more effective as an antimicrobial agent against S. gordonii (66.35%) than A. viscosus (34.13%) and co-cultures of both exhibited 29.9% inhibition.

TABLE 9

Effects of various treatments on the % inhibition of S. sobrinus and A. Viscosus.

| Bacterial species | % Inhibition | | | |
|---|---|---|---|---|
| | Naringin alone (0.5 mM) | Naringin:Zinc Complex (0.5 mM) | Naringin (0.325 mM) + Zinc acetate (0.175 mM) (0.5 mM total) | Zinc Acetate alone (0.175 mM) |
| S. sobrinus | −2.64 ± 2.54 | 84.30 ± 3.67 | 7.33 ± 4.23 | −1.05 ± 3.10 |
| A. viscosus | −3.50 ± 4.10 | 27.07 ± 1.88 | 7.78 ± 1.88 | −1.84 ± 5.86 |
| S. sobrinus/ A. viscosus | −3.79 ± 7.15 | 29.9 ± 0.67 | 0.32 ± 2.17 | 2.46 ± 6.58 |

The naringin:Zinc complex when added to single or co-cultured bacterium resulted in a synergistic inhibition of both single species and of co-cultures of bacteria. Naringin alone, in combination with Zinc acetate or Zinc acetate alone showed little to no detectable inhibition. Additionally, the complex appeared to exhibit differential effects on different species of bacteria. In this case, the complex at 0.5 mM is more effective as an antimicrobial agent against S. sobrinus (84.30%) than A. viscosus (27.07%/6) while co-cultures showed 29.9% inhibition.

TABLE 10

Effects of various treatments on the % inhibition of S. actinomycetemcomitans and A. Viscosus. The concentration of the sample treatment was chosen to mimic the stoichiometric ratio of 2:1 (Naringin to Zinc).

| Bacterial species | % Inhibition | | | |
|---|---|---|---|---|
| | Naringin alone (0.5 mM) | Naringin:Zinc Complex (0.5 mM) | Naringin (0.325 mM) + Zinc acetate (0.175 mM) (0.5 mM total) | Zinc Acetate alone (0.175 mM) |
| A. actinomycetemcomitans | 5.01 ± 1.69 | 56.47 ± 4.23 | 20.87 ± 0.42 | 29.24 ± 0.42 |
| A. viscosus | −3.50 ± 4.10 | 27.07 ± 1.88 | 7.78 ± 1.88 | −1.84 ± 5.86 |
| A. actinomycetemcomitans/ A. viscosus | −0.03 ± 2.02 | 37.52 ± 4.03 | 8.05 ± 2.01 | 4.13 ± 6.89 |

The naringin:Zinc complex when added to single or co-cultured bacterium resulted in a synergistic inhibition of both single species and of co-cultures of bacteria. Naringin alone, in combination with Zinc Acetate or Zinc Acetate alone showed little to no detectable inhibition. Additionally, the complex appeared to exhibit differential effects on different species of bacteria. In this case, the complex at 0.5 mM is more effective as an antimicrobial agent against A. actinomycetemcomitans (56.47%) than A. viscosus (27.07%) while co-cultures of both resulted in 37.52% inhibition.

TABLE 11

Effects of various treatments on the % inhibition of S. sobrinus and A. actinomycetemcomitans. The concentration of the sample treatment was chosen to mimic the stoichiometric ratio of 2:1 (Naringin to Zinc).

| Bacterial species | % inhibition | | | |
|---|---|---|---|---|
| | Naringin alone (0.5 nM) | Naringin:Zinc Complex (0.5 mM) | Naringin (0.325 mM) + Zinc acetate (0.175 mM) (0.5 mM total) | Zinc Acetate alone (0.175 mM) |
| S. sobrinus | −2.64 ± 2.54 | 84.30 ± 3.67 | 7.33 ± 4.23 | −1.05 ± 3.10 |
| A. actinomycetemcomitans | 5.01 ± 1.69 | 56.47 ± 4.23 | 20.87 ± 0.42 | 29.24 ± 0.42 |
| A. actinomycetemcomitans S. sobrinus | 0.33 ± 3.48 | 79.1 ± 0.54 | 9.42 ± 2.95 | 6.58 ± 5.36 |

The naringin:Zinc complex when added to single or co-cultured bacterium resulted in a synergistic inhibition of both single species and of co-cultures of bacteria. Naringin alone or in combination with Zinc Acetate or Zinc Acetate alone showed little to no detectable inhibition. Additionally, the complex appeared to exhibit differential effects on different species of bacteria. In this case, the complex at 0.5 mM was more effective as an antimicrobial agent against S. sobrinus (84.30%) than A. actinomycetemcomitans (56.47%) while co-cultures exhibited 79.1% inhibition.

As a positive control for the antimicrobial assay, the same species of bacteria cultures were treated with Triclosan in the range of 0.01%-1.7e-6% in 1% EtOH final concentration. The $IC_{50}$ was determined using GraphPad Prism version 6 software to be in the range of 0.00010-0.00027% (1-2.7 ppm).

The findings here show that the antimicrobial efficacy of naringin can be enhanced with the presence of metal zinc within as a naringin:Zinc complex or as a combination of Zinc and naringin. Surprisingly, the anti-microbial efficacy is enhanced with the naringin:Zinc complexes of the present invention, which are, at least partially, characterized by having 2:1 stoichiometric ratio of naringin to Zinc.

Figure 17:
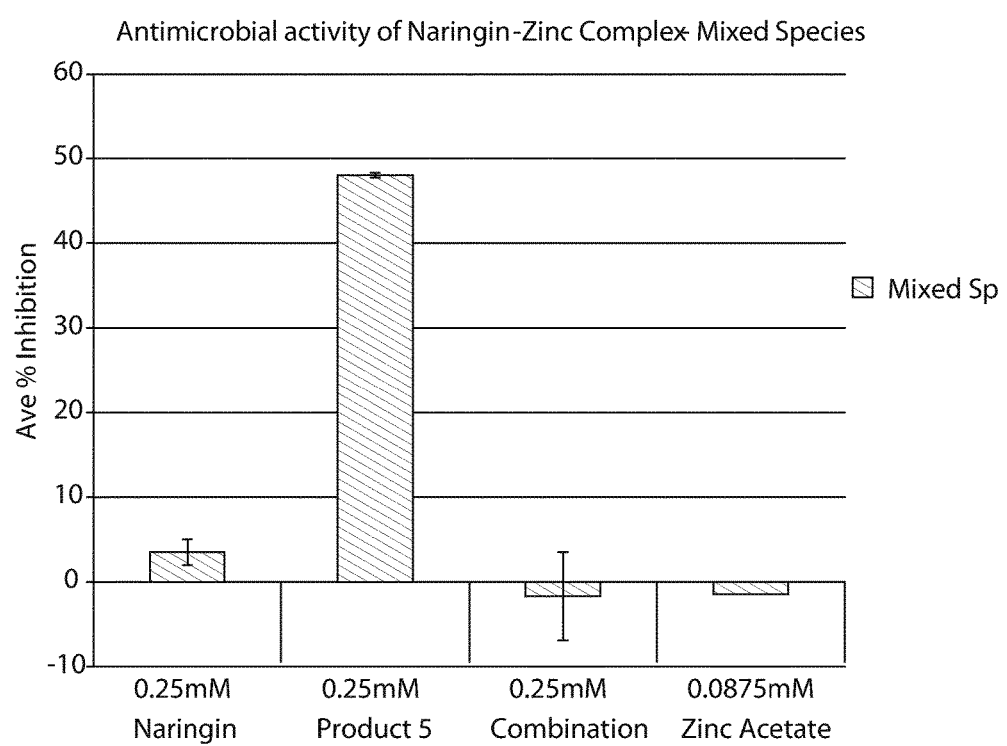
FIG. 17 shows the antimicrobial activity of naringin alone, 2:1 naringin:Zinc complex (Product 5), naringin+ Zinc acetate combination, and Zinc Acetate alone on mixed bacterial cultures at 37° C., 5% $CO_2$, anaerobic conditions ($OD_{610}$ 0.1).
Figure 18:
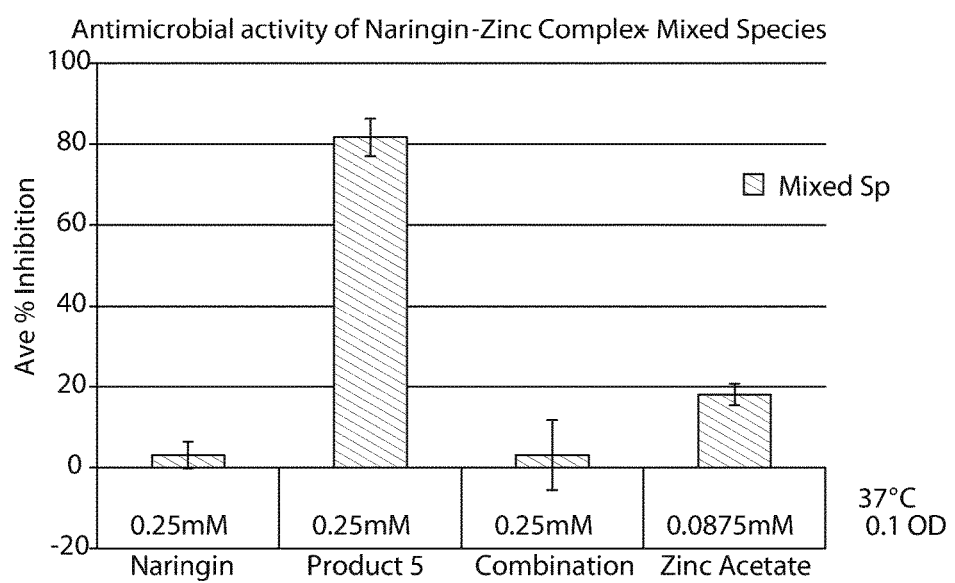
FIG. 18 shows the antimicrobial activity of naringin alone, 2:1 naringin:Zinc complex (Product 5), naringin+ Zinc acetate combination, and Zinc Acetate alone on mixed bacterial cultures at 37° C., aerobic conditions ($OD_{610}$ 0.1).

Using mixed species cultures, we observed that Naringin:Zinc complex resulted in a synergistic inhibition in comparison to naringin+Zinc combination and Zinc acetate alone regardless of whether the cultures were incubated with or without 5% $CO_2$ (see FIG. 17, FIG. 18, and Table 12). The antimicrobial efficacy of the complex was more potent against cultures incubated in the absence of 5% $CO_2$ (see Table 12).

TABLE 12

Summary of the effects of various treatments on mixed culture solutions.

| | % Inhibition | | | |
|---|---|---|---|---|
| Bacterial species and culturing conditions | Naringin alone (0.25 mM) | Naringin:Zinc Complex (0.25 mM) | Naringin (0.1625 mM) + Zinc acetate (0.0875 mM) (0.25 mM total) | Zinc Acetate alone (0.0875 mM) |
| Mixed species incubated in 37° C., 5% CO2 | 3.512 ± 1.53 | 48.244 ± 0.31 | −1.67 ± 5.20 | −1.46 ± 0.0 |
| Mixed species incubated in 37° C.; Air | 3.099 ± 3.31 | 81.70 ± 4.63 | 3.10 ± 8.60 | 18.07 ± 2.65 |

Antimicrobial characterization was also performed on mixed culture solutions having at least five microbial species present. A mixed culture containing *Actinomyces viscosus* (*A. viscosus*, A.v) (ATCC, #43146), *Lactobacillus casei* (*L. casei*, L.c) (ATCC #334), *Streptococcus oralis* (*S. oralis*, S.o) (ATCC #35037), *Fusobacterium nucleatum* (*F. nucleatum*, F.n) (ATCC #10953) and *Veilonella parvula* (*V. parvula*, V.p) (ATCC #17745) was maintained in a specialized complex medium (Modified BHI II Medium) in a continuous culture chemostat at 37° C. Approximately 10 ml of the culture was removed and the $OD_{610}$ was determined. The assay was performed using cultures at two concentrations; 0.03 and 0.1 at $OD_{610}$. Test samples (Naringin, Naringin:Zinc complex and Naringin+Zinc Acetate (combination)) were prepared as a 100 mM stock solution followed by 2 fold serial dilution in 100% DMSO. Triclosan (positive control) was prepared as a 10% stock in 100% EtOH and 3 fold serial dilutions were performed in 100% EtOH. Appropriate amount of the diluted samples were transferred into 96 well clear plate such that the resulting final concentration of Naringin alone, Naringin:Zinc complexes, Naringin+Zinc Acetate (combination) ranged from 2 mM to 0.0078 mM (2% DMSO) and Triclosan ranged from 0.01% to 1.7e-6% (1% EtOH), in 100 ul BH II media (Alvarez G. et al.; *AMB Express;* 2013, 3(1), doi: 10.1186/2191-0855-3-1) per well. For Naringin+Zinc acetate combination, while the highest total overall concentration was 2 mM, the exact concentration was Naringin (1.3 mM) and Zinc Acetate (0.7 mM) due to the compositions 2:1 molar ratio. For Zinc Acetate, in order to mimic the 2:1 ratio (ligand:Zinc) composition as in the complex, the final concentration range from 0.7 mM to 0.0027 mM in 2% DMSO was used instead.

A 100 µl of bacterial culture at chosen $OD_{610}$ (0.03 or 0.1) was introduced into the wells with the test samples. The wells were thoroughly mixed and plates incubated overnight in a 37° C. incubator with or without 5% $CO_2$. After approximately 12-13 hours of treatment, the plate was read using Envision plate reader (Serial #1040984), absorbance at 610 nm. The % inhibition relative to control was determined as described for previously described antimicrobial protocols, supra.

We observed that in the mixed species cultures irrespective of whether the cultures were incubated aerobically or anaerobically, the overall outcome is a synergistic antimicrobial effect in the presence of the complex, not their individual parts alone or in combination. However, in the aerobic condition, the antimicrobial efficacy of the complex is almost doubled that of the cultures in the anaerobic condition (81.7% vs 48.2%) for the same concentration tested.

For a positive control, the mixed species cultures were treated with Triclosan in the range of 0.01%-1.7e-6% in 1% EtOH. The $IC_{50}$ was determined, using GraphPad Prism version 6 software, to be in the range of 0.00014-0.00022% (1.4-2.2 ppm) (data not shown).

Example 14—Tissue Zinc Uptake Analysis

EpiGingival™ tissue models used for the zinc uptake study were purchased from MatTek Corporation (Ashland, Mass., cat #Gin-606). All samples were prepared in a final concentration of 1% DMSO in 7% of Propylene Glycol (PG). For example, 1 mM of naringin:Zinc complex was prepared in a final concentration of 1% DMSO and 7% PG; naringin and Zinc acetate combination was prepared such that the total concentration was 1 mM but consisted of 0.67 mM of naringin and 0.33 mM Zinc acetate in 1% DMSO and 7% PG. Zinc acetate was prepared at 0.33 mM to mimic the amount of zinc that is present in 1 mM of naringin:Zinc complex. For the vehicle only control, 1% DMSO in 7% PG was used. All samples were equilibrated to 37° C. prior to testing.

Zinc uptake studies were performed using EpiGingival™ tissue models from MatTek Corporation. Briefly, EpiGingival™ tissue inserts were equilibrated overnight in 1 ml of the EpiGingival™ assay media (supplied by MatTek Corporation). For testing, working with one insert at a time, the insert was removed and placed inside a clean 6 well plate. Then, 1 ml of the test sample was carefully removed and introduced to the inside of the insert and allowed to incubate for 2 minutes. Next, the samples were removed using an aspirator and the tissue rinsed with 1 ml of warm water (37° C.). This was repeated for 2 more times for a total of 3 washes. At the end of the last wash making sure to remove as much of the water as possible, the tissue was disengaged from the insert with the tip of a sterile forceps, and transferred into a clean 15 ml Falcon tube. The process was repeated until all the tissues were treated. Experiments were performed three times with each test sample assayed in duplicate.

Digestion of Tissues: Briefly, 0.5 ml of a mixture of 7:3 HCl/HNO$_3$ was introduced into a 15 ml Falcon tube containing one of the treated tissue samples and allowed to digest overnight. The following day, 4.5 ml of water was added to each of the digested tissue samples, thoroughly mixed and centrifuged at 4,000 RPM for 10 minutes at room temperature. The clear supernatant (4.5 ml) was transferred into a clean, labeled Falcon tube and submitted for analytical analysis of Zinc.

Figure 19:
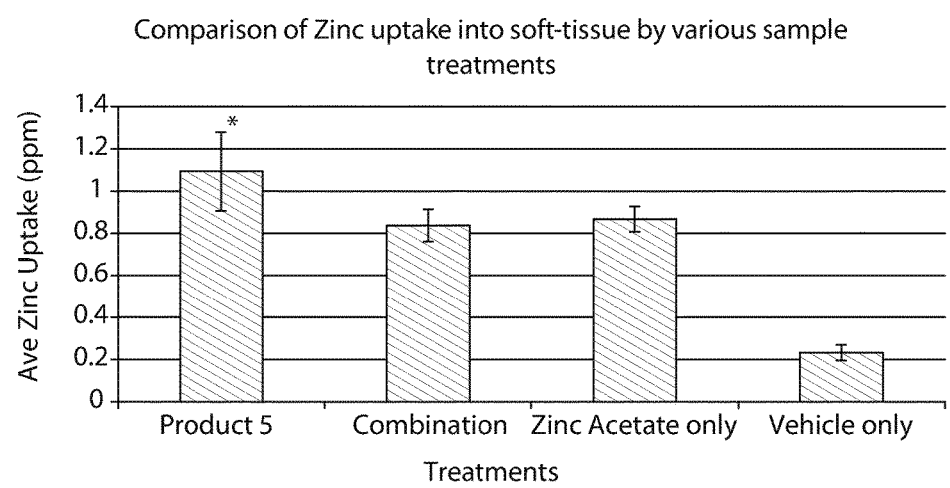
FIG. 19 is a comparison of zinc update into soft-tissue when treated with 2:1 naringin:Zinc complex (Product 5), naringin+Zinc acetate combination, Zinc Acetate alone or vehicle alone. *–p<0.005.

Average zinc uptake (ppm) and the standard deviation of samples were calculated using Microsoft Excel 2010. A one way ANOVA was done to determine the p value. A plot of the average zinc (ppm) against the various treatments was generated (see FIG. 19).

Naringin:Zinc complex (Product 5) exhibited a significant zinc uptake in comparison to the naringin+Zinc acetate combination at the same molar concentration. By contrast, zinc uptake by Product 5 was determined to be not significantly different from that by Zinc Acetate alone at the same molar concentration. The zinc uptake and the antimicrobial characteristics taken together, without being bound to theory, suggest the observed synergistic antimicrobial effect may be a reflection of the complex as a whole rather than zinc acetate alone.

TABLE 13

Summary of Zinc uptake from EpiGingival ™ tissue models after 2 minute treatment with Naringin:Zinc complex (Product 5), combination of naringin and Zinc acetate and Zinc acetate alone.

| | Zn (ppm) | | | | | | | |
| --- | --- | --- | --- | --- | --- | --- | --- | --- |
| | Preparation 1 | | Preparation 2 | | Preparation 3 | | Ave | |
| Samples | N1 | N2 | N1 | N2 | N1 | N2 | (ppm) | STDEV |
| Product 5 | 0.94 | 0.82 | 1.22 | 1.31 | 1.07 | 1.2 | 1.09 | 0.19 |
| Naringin + Zinc acetate | 0.93 | 0.86 | 0.91 | 0.81 | 0.75 | 0.76 | 0.84 | 0.08 |
| Zinc acetate only | 0.96 | 0.92 | 0.82 | 0.81 | 0.84 | 0.85 | 0.87 | 0.06 |
| Vehicle only | 0.2 | 0.22 | 0.3 | 0.24 | 0.23 | 0.2 | 0.23 | 0.04 |

Preparation 1, 2 and 3 refers to three different synthesized batches of Product 5. Each experiment was performed in duplicate (N1 and N2); Zn refers to Zinc in parts per million (ppm).

Example 15—Synthesis Method 6

Two moles Naringin (1.21 g.) and one mole ZnO (0.081 g.) was mixed in 100 ml H$_2$O. The solution was heated to 80° C. for 4 hours with vigorous stirring. A yellowish powder was formed (1.102 g., 90%0, yield). The powder was washed with hot water (3×100 ml). Mixing 21.4 mg of the powder in 10% HNO$_3$ produced a clear solution. The product, labeled as Product 7, was characterized using FTIR, $^1$H-NMR and Diffusion Ordered Spectroscopy.

Example 16—Wound Healing

Cell Culture: Spontaneously immortalized human keratinocyte line, HaCaT cells (AddexBio, San Diego, Calif., cat #T0020001) were cultured in 25 cm$^2$ vented, Falcon canted tissue culture flasks (VWR, Radnor, Pa., cat #353108) using complete DMEM media (Life Technologies, Grand Island, N.Y., cat #11965-092) supplemented with 10% characterized Hyclone FBS (VWR, Radnor, Pa., cat #1677-014) and 1× Penicillin—Streptomycin (Life Technologies, Grand Island, N.Y., cat #15140122). The cultures were incubated at 37° C. and 5% CO$_2$ until the cells reached around 70-80% confluence. Cells were then detached with Trypsin—EDTA solution (Sigma, St. Louis, Mo., cat #T3924) and used either for propagation or in experimentation.

Assay sample preparation: Samples were prepared in a final concentration of 1% DMSO in complete media. The following were prepared—naringin at 0.1 mM, naringin:zinc complex at 0.15 mM, Zinc acetate at 0.05 mM and naringin+Zinc acetate combination at a final concentration of 0.15 mM. 1% DMSO in complete media was used as a vehicle control and media alone as the positive control. Each treatment was done in quadruplets and the average was taken. Two different batches of product 5 were tested at 0.15 mM, the average % Growth Relative to day 0 (d0) was determined and presented in FIG. 20.

Preparation of wound: HaCaT cells at around 70-80% confluence were treated with 1 ml of Trypsin-EDTA solution and incubated at 37° C., 5% CO$_2$ until the cells detached from the flask. 5 ml of the complete media were added to stop further trypsinization of the cells. The cell suspensions were transferred into a clean 50 ml Falcon centrifuge tube and spun down at 1500 RPM for 5 minutes to pellet the cells. Pelleted cells were re-suspended in 50 ml of fresh complete media and 1 ml of the cell suspensions was transferred into each well of a Falcon 353047 24-well plate (VWR, Radnor, Pa.). The plates were incubated at 37° C., 5% CO2 until cells reached around 90% confluence.

Figure 21:
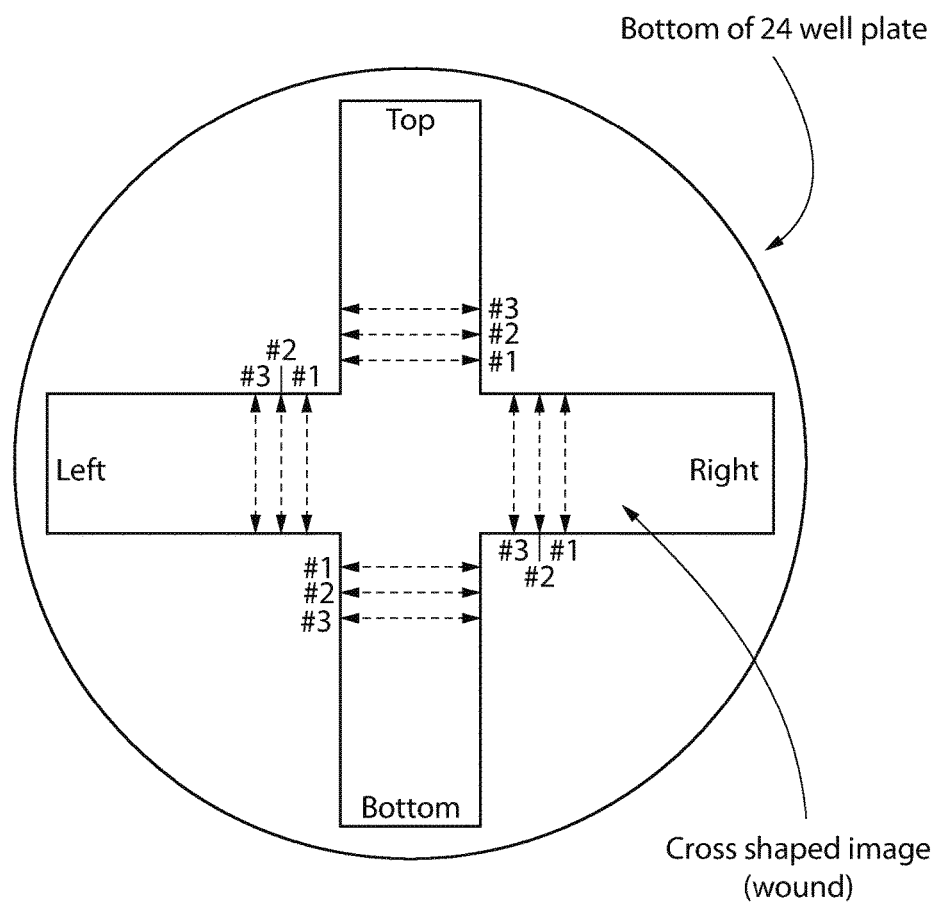
FIG. 21 is a diagram showing the crossed-shaped image created in the cell monolayer to simulate a wound.

On the day of the assay, a "crossed-shaped image" was aseptically created onto the bottom of each of 24 well plate cell monolayers using a sterile p1000 pipette tip to simulate a "wound" (see FIG. 21). The cells were washed twice with 1 ml of plain media with gentle shaking for a minute and then refreshed with 1 ml of appropriate test media.

Quantifying cell migration/wound healing: To explore the effects of various actives on cell migration/wound healing, the size of the freshly generated wound (the gap size) was determined following treatment using an inverted microscope (Olympus 1X71, Olympus Scientific Solutions Americas, Waltham, Mass.) and Cellsens Dimension 1.11 (Olympus Corporation, Waltham, Mass.) software and monitored until the gap closed completely. Three different measurements were taken for each arm of the "crossed" wound image. A total of 12 measurements were taken for each of the 24 well (3 readings from the top, 3 from the bottom, 3 from the right and remaining 3 from the left) (see FIG. 21). The mean of each arm was determined for each day of the study until the wound heal and no gap existed. The % of cell growth relative to d0 (day 0) for each treatment was calculated as follows:

$$\% \text{ Growth relative to } d0 = \frac{\text{measurement of gap at } d0 - \text{measurement of gap post treatment}}{\text{measurement of gap at } d0} \times 100\%$$

Figure 20:
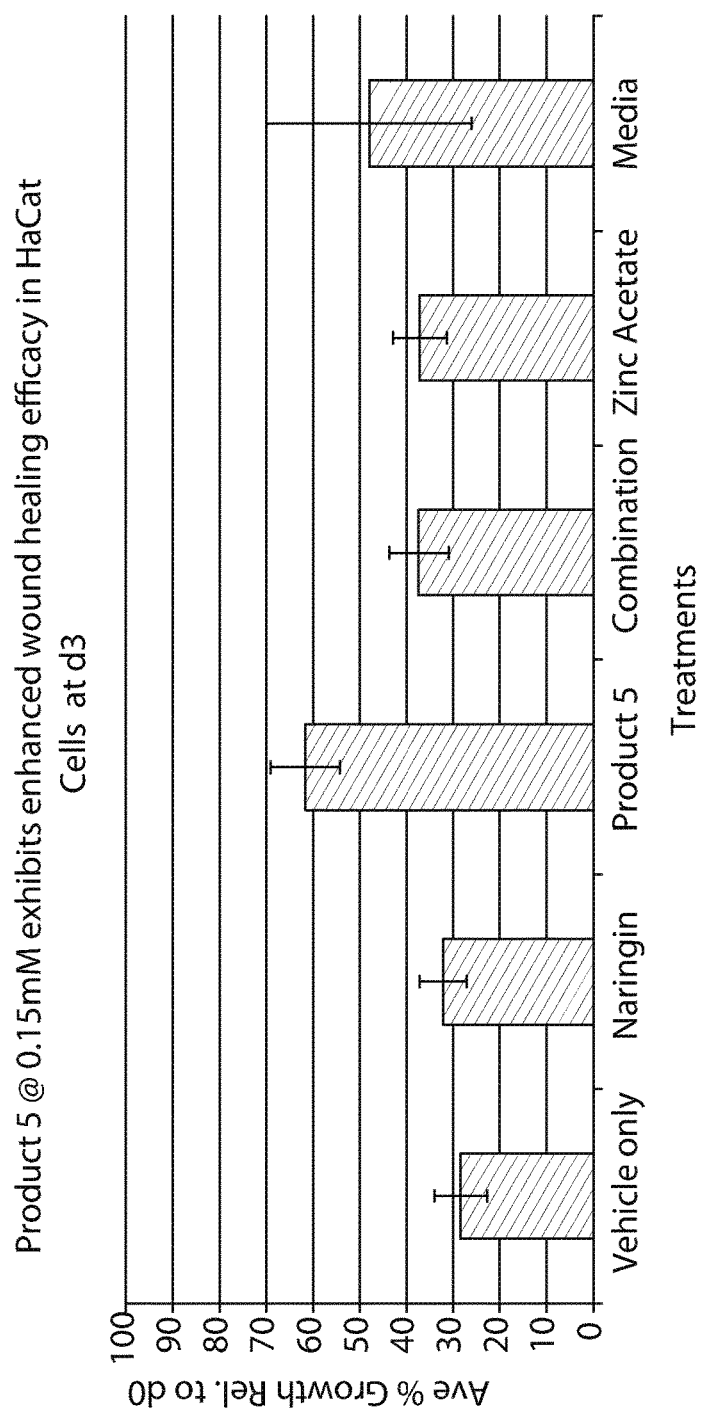
FIG. 20 is a comparison of the effects of various treatments in cell migration/proliferation "wound healing" in a scratch assay using HaCat cells.

Results: As shown in FIG. 20, treatment with Product 5 resulted in an enhanced "wound healing" when compared to naringin treatment alone, Zinc acetate alone as well as the combination of naringin and Zinc acetate. Naringin treatment alone was not significantly different from that of Zinc acetate, the combination of both naringin and Zinc acetate, vehicle alone as well as the media treatment. Comparing media to vehicle alone showed inhibition of growth in vehicle treated wells (possibly due to the presence of DMSO). Surprisingly, cells treated with Product 5 were able to recover much better than individual components alone or in combination. Similar findings were observed with 0.20 mM of Product 5 (data not shown).

While the present invention has been described with reference to embodiments, it will be understood by those skilled in the art that various modifications and variations may be made therein without departing from the scope of the present invention.

What is claimed is:

1. A naringin:Zn complex, wherein said naringin:Zn complex has a 2:1 naringin to zinc molar ratio.
2. The naringin:Zn complex of claim 1, wherein said complex has a melting point above 230° C.
3. The naringin:Zn complex of claim 1, wherein said naringin:Zn complex has a diffusion coefficient between 2.8e-11 to 3.2e-11 $m^2$/s in DMSO solution at 25° C.
4. An oral care composition comprising the naringin:Zinc complex of claim 1.
5. The oral care composition of claim 4, wherein the oral care composition may be any of the following selected from the group consisting of: a toothpaste or a dentifrice, a mouthwash or a mouth rinse, a topical oral gel and a denture cleanser.
6. The composition claim 1, wherein said composition further comprises one or more agents selected from diluents, bicarbonate salts, pH modifying agents, surfactants, foam modulators, additional thickening agents, humectants, sweeteners; flavorants, pigments, antibacterial agents, anticaries agents, fluoride ion sources, anticalculus or tartar control agents, and mixtures thereof.
7. A method to improve oral health comprising applying an effective amount of the oral composition of claim 1 to the oral cavity of a subject in need thereof.
8. The method of claim 7, wherein improving oral health may be selected from one or more of the following;
   a. reduce or inhibit formation of dental caries;
   b. reduce, repair or inhibit early enamel lesions;
   c. reduce or inhibit demineralization and promote remineralization of the teeth;
   d. reduce hypersensitivity of the teeth;
   e. reduce or inhibit gingivitis;
   f. promote healing of sores or cuts in the mouth;
   g. reduce levels of acid producing bacteria;
   h. to increase relative levels of arginolytic bacteria;
   i. inhibit microbial biofilm formation in the oral cavity;
   j. raise and/or maintain plaque pH at levels of at least pH 5.5 following sugar challenge;
   k. reduce plaque accumulation;
   l. treat, relieve or reduce dry mouth;
   m. whiten teeth;
   n. enhance systemic health, including cardiovascular health;
   o. reduce erosion of the teeth;
   p. immunize the teeth against cariogenic bacteria and their effects;
   q. clean the teeth and oral cavity;
   r. reduce inflammation; and
   s. increase anti-oxidant levels.
9. A method of preparing a naringin:Zn complex having a 2:1 naringin to zinc molar ratio.
10. The method of claim 9, wherein said complex is prepared using a pH between 7-10.
11. The method of claim 9, wherein mixing of naringin and zinc is performed at a temperature between 65-85° C.
12. The method of claim 9, wherein preparation of said complex comprises the steps of:
   a. mixing naringin in methanol;
   b. adding a source of zinc;
   c. adjusting the pH of the solution to 10.0;
   d. incubating the reaction; and
   e. optionally isolating said complex.
13. The method of claim 9, wherein preparation of said complex comprises the steps of:
   a. mixing naringin in water;
   b. heating the mixture to 70° C.;
   c. adding a source of zinc;
   d. adjusting the pH of the solution to 10.0;
   e. incubating the reaction; and
   f. optionally isolating said complex.
14. The method of claim 9, wherein preparation of said complex comprises the steps of:
   a. mixing naringin in water;
   b. heating the mixture to 70° C.;
   c. adjusting the pH of the solution to 10.0;
   d. adding a source of zinc; and
   e. optionally isolating said complex.
15. The method of claim 9, wherein preparation of said complex comprises the steps of:
   a. mixing naringin in water;
   b. heating the mixture to 70° C.;
   c. adding a source of zinc;
   d. adjusting the pH of the solution to 7.0; and
   e. optionally isolating said complex.
16. The method of claim 9, wherein preparation of said complex comprises the steps of:
   a. mixing naringin in propylene glycol at 70° C.;
   b. adjusting the pH of the solution to be between 9.0-10.0;
   c. adding a source of zinc in propylene glycol at 70° C.; and
   d. optionally isolating said complex.
17. The method of claim 12, wherein said Zn source is selected from zinc acetate, zinc oxide, zinc chloride, zinc lactate, zinc citrate, or zinc nitrate.
18. The method of claim 17, wherein said Zn source is zinc acetate.
19. The method of claim 9, wherein ZnO is used as a source of Zn for the reaction.
20. The method of claim 19, said method comprises the steps of:
   a. mixing naringin and ZnO in water;
   b. heating the mixture;
   c. incubating the mixture; and
   d. optionally isolating said complex.

* * * * *